(12) United States Patent
Wiechmann et al.

(10) Patent No.: US 10,390,994 B2
(45) Date of Patent: Aug. 27, 2019

(54) TREATMENT APPARATUS FOR SURGICAL CORRECTION OF DEFECTIVE EYESIGHT, METHOD OF GENERATING CONTROL DATA THEREFORE, AND METHOD FOR SURGICAL CORRECTION OF DEFECTIVE EYESIGHT

(71) Applicant: Carl Zeiss Meditec AG, Jena (DE)

(72) Inventors: Martin Wiechmann, Jena (DE); Michael Bergt, Weimar (DE); Mark Bischoff, Jena (DE); Markus Sticker, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 16/160,490

(22) Filed: Oct. 15, 2018

(65) Prior Publication Data
US 2019/0110922 A1    Apr. 18, 2019

Related U.S. Application Data

(62) Division of application No. 15/184,363, filed on Jun. 16, 2016, now Pat. No. 10,098,784, which is a
(Continued)

(51) Int. Cl.
*A61B 34/10* (2016.01)
*A61F 9/008* (2006.01)

(52) U.S. Cl.
CPC .............. *A61F 9/008* (2013.01); *A61B 34/10* (2016.02); *A61F 9/00829* (2013.01);
(Continued)

(58) Field of Classification Search
CPC ................................ A61F 9/008; A61B 34/10
(Continued)

(56) References Cited

U.S. PATENT DOCUMENTS

| 4,907,586 A | 3/1990 | Bille et al. |
| 5,049,147 A * | 9/1991 | Danon .................. A61B 18/20 606/10 |

(Continued)

FOREIGN PATENT DOCUMENTS

| DE | 695 00 997 T2 | 4/1998 |
| DE | 103 34 109 A1 | 2/2005 |

(Continued)

OTHER PUBLICATIONS

Intralase Product Leaflet, Essential Technology for Biomechanical Stability, Intralase Corp., 2006, 6 pages.
(Continued)

*Primary Examiner* — John R Downey
(74) *Attorney, Agent, or Firm* — Patterson Thuente Pederson, P.A.

(57) ABSTRACT

A treatment method and apparatus for surgical correction of defective-eyesight in an eye of a patient, wherein a laser device is controlled by a control device, said laser device separating corneal tissue by irradiation of laser radiation to isolate a volume located within a cornea, wherein the control device controls the laser device to focus the laser radiation, by providing target points located within the cornea, into the cornea, wherein the control device, when providing the target points, allows for focus position errors which lead to a deviation between the predetermined position and the actual position of the target points when focusing the laser radiation, by pre-offsets depending on the positions of the respective target points to compensate for said focus position errors.

41 Claims, 9 Drawing Sheets

Related U.S. Application Data division of application No. 14/182,074, filed on Feb. 17, 2014, now Pat. No. 9,370,445, which is a division of application No. 11/937,955, filed on Nov. 9, 2007, now Pat. No. 8,685,006.

(60) Provisional application No. 60/858,201, filed on Nov. 10, 2006.

(52) U.S. Cl.
CPC .. *A61F 9/00838* (2013.01); *A61F 2009/0088* (2013.01); *A61F 2009/00848* (2013.01); *A61F 2009/00851* (2013.01); *A61F 2009/00872* (2013.01); *A61F 2009/00878* (2013.01); *A61F 2009/00882* (2013.01); *A61F 2009/00897* (2013.01)

(58) Field of Classification Search
USPC .......................................................... 606/4–6
See application file for complete search history.

(56) References Cited

U.S. PATENT DOCUMENTS

| | | | |
|---|---|---|---|
| 5,549,632 A | 8/1996 | Lai | |
| 5,634,919 A * | 6/1997 | Azar | A61F 9/008 606/10 |
| 5,656,186 A | 8/1997 | Mourou et al. | |
| 5,807,379 A | 9/1998 | L'Esperance, Jr. | |
| 5,984,916 A | 11/1999 | Lai | |
| 5,993,438 A | 11/1999 | Juhasz et al. | |
| 6,030,376 A * | 2/2000 | Arashima | A61B 3/113 606/12 |
| 6,033,075 A | 3/2000 | Fujieda et al. | |
| 6,099,522 A | 8/2000 | Knopp et al. | |
| 6,110,166 A * | 8/2000 | Juhasz | A61F 9/008 128/898 |
| 6,129,722 A * | 10/2000 | Ruiz | A61F 9/008 351/212 |
| 6,149,643 A * | 11/2000 | Herekar | A61F 9/008 606/10 |
| 6,159,205 A | 12/2000 | Herekar et al. | |
| 6,210,169 B1 * | 4/2001 | Yavitz | G09B 23/28 434/271 |
| 6,312,422 B1 | 11/2001 | Dubnack | |
| 6,325,792 B1 | 12/2001 | Swinger et al. | |
| RE37,585 E | 3/2002 | Mourou et al. | |
| 6,413,251 B1 * | 7/2002 | Williams | A61F 9/00806 128/898 |
| 6,416,179 B1 * | 7/2002 | Lieberman | A61F 9/00804 351/212 |
| 6,582,078 B2 | 6/2003 | Halpern | A61F 9/008 351/205 |
| 6,623,476 B2 | 9/2003 | Juhasz et al. | |
| 6,730,074 B2 * | 5/2004 | Bille | A61F 9/00825 128/898 |
| 6,887,231 B2 * | 5/2005 | Mrochen | A61F 9/00806 606/10 |
| 7,044,944 B2 * | 5/2006 | Campin | A61B 3/1015 128/898 |
| 2002/0075451 A1 | 6/2002 | Ruiz | |
| 2002/0077797 A1 | 6/2002 | Hall | |
| 2002/0082629 A1 | 6/2002 | Cox et al. | |
| 2003/0014042 A1 | 1/2003 | Juhasz et al. | |
| 2003/0055412 A1 * | 3/2003 | Lieberman | A61F 9/00804 606/5 |
| 2003/0069566 A1 | 4/2003 | Williams et al. | |
| 2003/0078753 A1 * | 4/2003 | Campin | A61B 3/1015 702/124 |
| 2004/0070761 A1 | 4/2004 | Horvath et al. | |
| 2004/0243112 A1 | 12/2004 | Bendett et al. | |
| 2005/0085800 A1 | 4/2005 | Lenzner et al. | |
| 2005/0159733 A1 * | 7/2005 | Dick | A61B 3/1015 606/5 |
| 2006/0155265 A1 | 7/2006 | Juhasz et al. | |
| 2006/0195075 A1 | 8/2006 | Muhlhoff et al. | |
| 2007/0027438 A1 * | 2/2007 | Loesel | A61F 9/008 606/4 |
| 2007/0027439 A1 * | 2/2007 | Durrie | A61F 9/008 606/5 |
| 2007/0179478 A1 | 8/2007 | Dobschal et al. | |
| 2007/0179483 A1 | 8/2007 | Muhlhoff et al. | |
| 2007/0193987 A1 | 8/2007 | Bischoff et al. | |
| 2007/0237620 A1 | 10/2007 | Muhlhoff et al. | |
| 2007/0293851 A1 * | 12/2007 | Muhlhoff | A61F 9/008 606/11 |
| 2008/0021443 A1 | 1/2008 | Bischoff et al. | |
| 2012/0016351 A1 * | 1/2012 | Stobrawa | A61F 9/008 606/5 |
| 2012/0035598 A1 * | 2/2012 | Stobrawa | A61F 9/008 606/5 |

FOREIGN PATENT DOCUMENTS

| | | |
|---|---|---|
| DE | 103 58 927 A1 | 7/2005 |
| DE | 10 2004 014 181 A1 | 10/2005 |
| EP | 0 754 103 B1 | 11/1997 |
| EP | 1 153 584 A1 | 11/2001 |
| EP | 1 159 986 A2 | 12/2001 |
| EP | 1 719 483 A1 | 11/2006 |
| WO | WO 93/08677 | 5/1993 |
| WO | WO 96/11655 | 4/1996 |
| WO | WO 99/38443 | 8/1999 |
| WO | WO 03/002008 A1 | 1/2003 |
| WO | WO 2004/032810 A2 | 4/2004 |
| WO | WO 2005/011545 A1 | 2/2005 |
| WO | WO 2005/011546 A1 | 2/2005 |
| WO | WO 2005/011547 A1 | 2/2005 |
| WO | WO 2005/048895 A1 | 6/2005 |
| WO | WO 2005/079717 A1 | 9/2005 |
| WO | WO 2005/092172 A1 | 10/2005 |
| WO | WO 2007/109399 A1 | 9/2007 |

OTHER PUBLICATIONS

Extended European Search Report for European Patent Application No. 10173881.3, dated Dec. 8, 2010.

Application and File History for U.S. Appl. No. 11/937,955, filed Nov. 9, 2007. Inventors: Martin Wiechmann et al.

Application and File History for U.S. Appl. No. 14/182,074, filed Feb. 7, 2014. Inventors: Martin Wiechmann et al.

Application and File History for U.S. Appl. No. 15/184,363, filed Jun. 16, 2016. Inventors: Martin Wiechmann et al.

* cited by examiner

FIG. 1
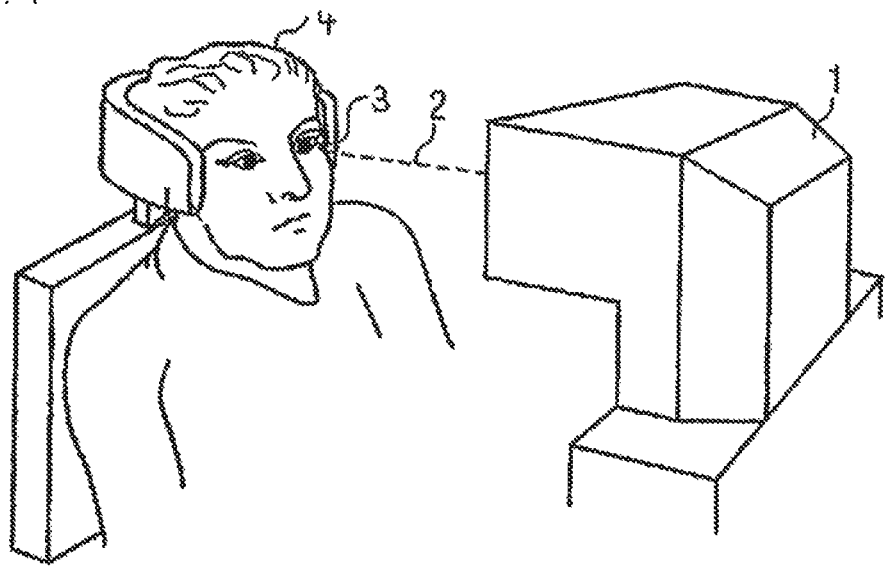
FIG. 2
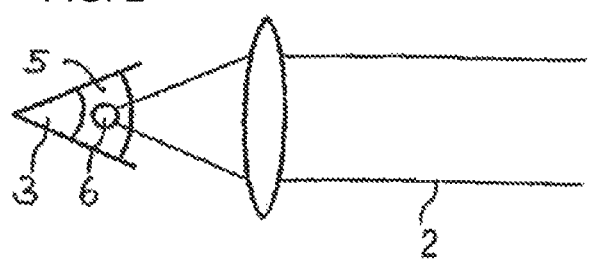
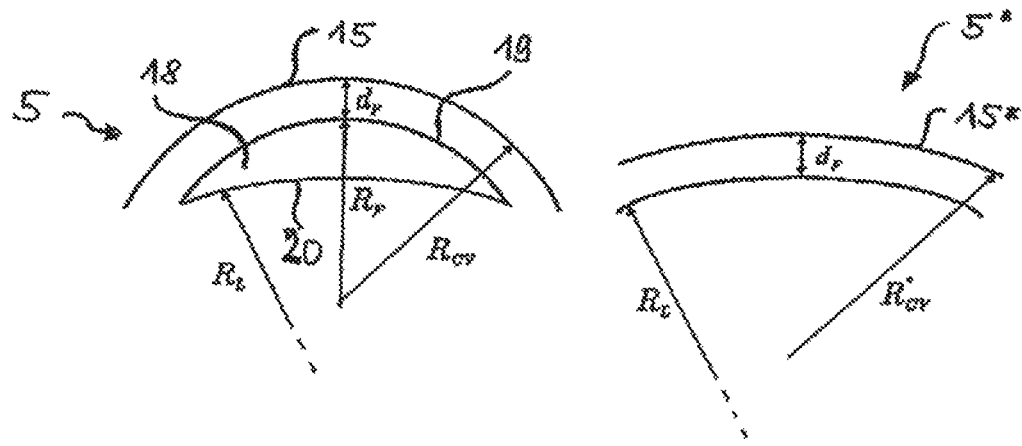
FIG. 5    FIG. 6

FIG. 3
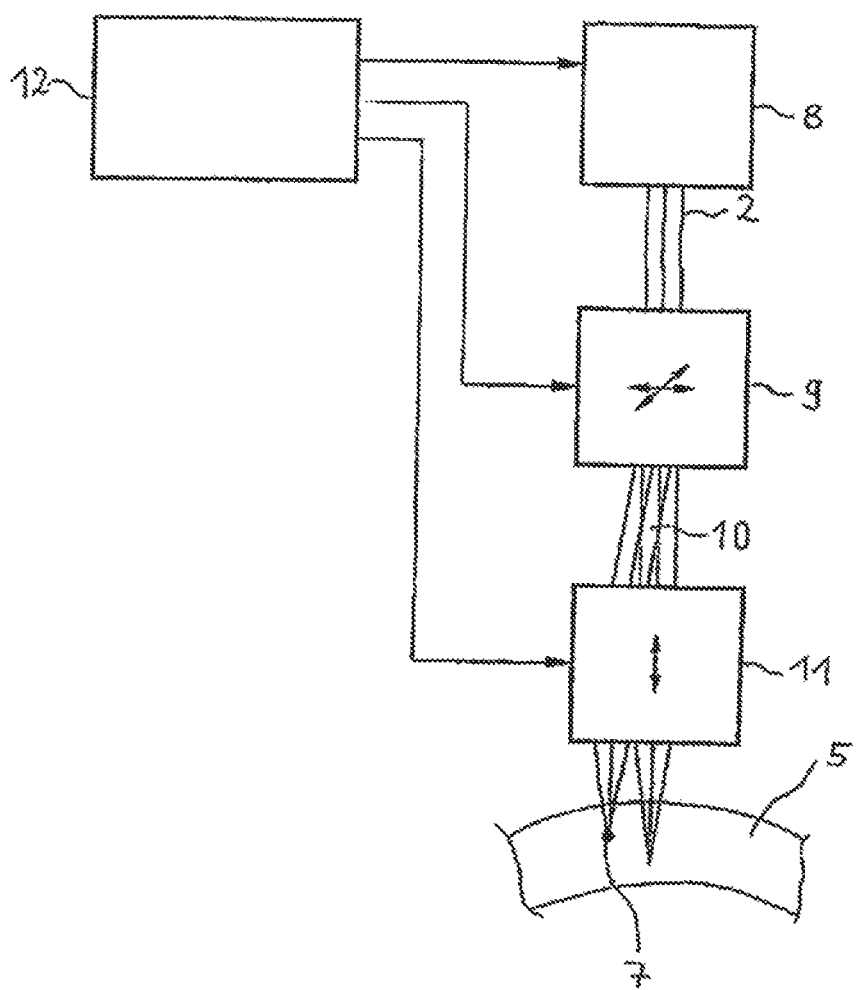
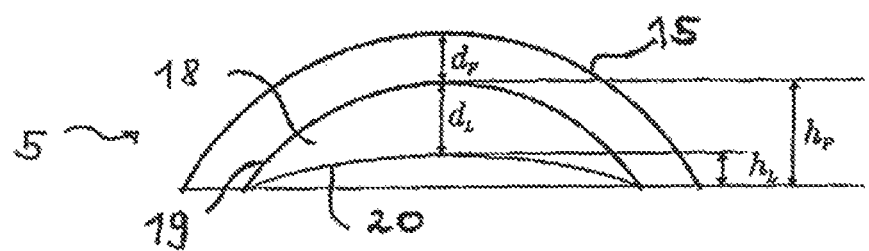
FIG. 7

TREATMENT APPARATUS FOR SURGICAL CORRECTION OF DEFECTIVE EYESIGHT, METHOD OF GENERATING CONTROL DATA THEREFORE, AND METHOD FOR SURGICAL CORRECTION OF DEFECTIVE EYESIGHT

CROSS-REFERENCE TO RELATED APPLICATIONS

This application is a divisional of application Ser. No. 15/184,363, filed Jun. 16, 2016, entitled "Treatment Apparatus for Surgical Correction of Defective Eyesight, Method of Generating Control Data Therefore, and Method for Surgical Correction of Defective Eyesight", which in turn is a divisional of application Ser. No. 14/182,074, filed Feb. 17, 2014, now U.S. Pat. No. 9,370,445, issued Jun. 21, 2016, entitled "Treatment Apparatus for Surgical Correction of Defective Eyesight, Method of Generating Control Data Therefore, and Method for Surgical Correction of Defective Eyesight", which in turn is a divisional of application Ser. No. 11/937,955, filed Nov. 9, 2007, entitled "Treatment Apparatus for Surgical Correction of Defective Eyesight, Method of Generating Control Data Therefore, and Method for Surgical Correction of Defective Eyesight", now U.S. Pat. No. 8,685,006, issued Apr. 1, 2014, which claims the benefit of U.S. Provisional Application No. 60/858,201, filed Nov. 10, 2006, entitled "Treatment Apparatus for Surgical Correction of Defective Eyesight, Method of Generating Control Data Therefore, and Method for Surgical Correction of Defective Eyesight", each of which is hereby fully incorporated herein by reference.

INVENTION PART A

The invention relates to a planning device for determining control data for a treatment apparatus for surgical correction of defective eyesight of a patient's eye, said planning device generating control data for the treatment apparatus comprising a laser device, which separates corneal tissue by irradiation of pulsed laser radiation, said laser radiation being focused on target points arranged in a pattern in the cornea.

The invention further relates to a treatment apparatus for surgical correction of defective eyesight of a patient's eye, said apparatus comprising an interface for supplying measurement data relating to parameters of the eye and defective-eyesight data relating to the eyesight defect to be corrected in the eye, and a laser device, which separates corneal tissue by irradiation of pulsed laser radiation, said laser radiation being focused on target points arranged in a pattern in the cornea.

Further, the invention relates to a method of preparing control data for a treatment apparatus for surgical correction of defective eyesight of a patient's eye, which apparatus comprises a laser device separating corneal tissue by irradiation of pulsed laser radiation, said laser device being operative to focus the laser radiation, according to the control data, on target points arranged in a pattern in the cornea.

Spectacles have long since been the classic way to correct defective eyesight of the human eye. Meanwhile, however, increasing use is made of refractive surgery which causes a correction of defective eyesight by modifications of the cornea. All surgical methods aim to selectively modify the cornea so as to influence light refraction. Several surgical methods are known for this purpose. The most widespread of these is the so-called laser in situ keratomileusis, also abbreviated as LASIK. In this method, a corneal lamella (or flap) is first created on one side from the corneal surface and folded aside. This lamella can be created using a mechanical microkeratome or a so-called laser keratome as distributed by Intralase Corp., Irvine, USA, for example.

The latter produces a cut in the cornea by laser radiation. In doing so, several processes take place in the tissue in a time sequence, which are initiated by the laser radiation. If the power density of the radiation exceeds a threshold value, an optical breakthrough forms, which produces a plasma bubble in the cornea. Said plasma bubble grows due to expanding gases after the optical breakthrough has formed. If the optical breakthrough is not maintained, the gas generated in the plasma bubble will be absorbed by the surrounding material and the bubble will disappear again. Tissue-separating effects acting without a plasma bubble are also possible. For the sake of simplicity, all such processes are summarized here by the term "optical breakthrough", i.e., this term is intended to include not only the actual optical breakthrough, but also the effects resulting therefrom in the cornea.

In order to generate the optical breakthrough, the laser radiation is applied in a pulsed manner, with the pulse duration being less than 1 ps. The required power density of the respective pulse for causing an optical breakthrough is thus generated only in a tiny spatial region. In this respect, U.S. Pat. No. 5,984,916 clearly shows that the spatial region of the optical breakthrough (of the interaction produced in this case) depends strongly on the pulse duration. Thus, high focusing of the laser beam in combination with the aforementioned short pulses allows the optical breakthrough to be placed in the cornea with pinpoint accuracy.

Now, in order to generate the thin flap, a series of optical breakthroughs is generated by the laser keratome at predetermined locations so as to form a cut surface which detaches the lamella from the underlying cornea.

Once the flap has been created and folded aside, the LASIK operation provides for application of an excimer laser which uses ablation to remove the corneal tissue thus exposed. With volume located in the cornea having been evaporated in this manner, the corneal lamella is folded back in its initial place. Thus, the LASIK method already in use which, when using a laser keratome is also referred to as fs LASIK, creates a lid-shaped corneal lamella, folds it away and ablates the tissue thus exposed using an ablation laser.

The prior art also mentions that the correction of defective eyesight is achieved by isolating a lens-shaped partial volume in the corneal tissue using the pulsed laser radiation. A corresponding description can be found, for example, in WO 2005/011545 A1. Accordingly, however, devices are not yet available in the market.

In the LASIK method the corneal tissue exposed by the keratome is ablated by an ablation laser such that a desired volume is removed thereby. For this purpose, the laser beam is focused on the exposed cornea in different places so as to remove the material. The material removal in the cornea is set by a so-called shot file, which determines the number of pulses of the ablation laser radiation and their respective coordinates onto which the pulses are emitted. The shot file is created in the devices after previous measuring of the eye. Due to its different principle of operation, the shot file is not suitable for the surgical methods and devices presently under scientific examination, which methods and devices isolate a volume in the cornea.

Therefore, it is an object of the invention to provide a planning device, an apparatus and/or a method of the above-mentioned type allowing easy surgical correction of defective eyesight by isolating a volume located in the cornea by means of laser radiation.

According to the invention, this object is achieved by a planning device of the above-mentioned type, which uses supplied measurement and defective-eyesight data to define a volume located within the cornea and whose removal from the cornea causes the desired correction of defective eyesight, said device determining a boundary surface which confines the defined volume within the cornea and generates for this boundary surface a control dataset for controlling the laser device, said dataset determining a three-dimensional pattern of target points located in the boundary surface and arranged such that the boundary surface is provided as a cut surface upon irradiation of the pulsed laser radiation according to the control data set, which cut surface isolates the defined volume in the cornea and, thus, makes it removable.

According to the invention, the object is also achieved by a treatment apparatus for surgical correction of defective eyesight of a patient's eye, said apparatus comprising an interface for supplying measurement data relating to parameters of the eye and defective-eyesight data relating to the eyesight defect to be corrected in the eye; a laser device, which separates corneal tissue by irradiation of pulsed laser radiation, said laser radiation being focused on target points arranged in a pattern in the cornea, and a planning device of the type described in the preceding paragraph.

The object is further achieved by a method of the above-mentioned type, which comprises the following steps: determining measurement data on parameters of the eye and defective-eyesight data on eyesight defects to be corrected in the eye; defining a volume based on the measurement data and the defective-eyesight data, which volume is located within the cornea and whose removal from the cornea upon operation of the treatment apparatus results in the desired correction of defective eyesight; determining a boundary surface which confines the defined volume within the cornea; determining a three-dimensional pattern of target points in the cornea, said target points being located in the boundary surface and being arranged such that the boundary surface is provided as a cut surface upon irradiation of the pulsed laser radiation according to the control data, said cut surface isolating the defined volume in the cornea and making it removable in this way; and creating a control data set which contains three-dimensional patterns for controlling the laser device.

According to the invention, a volume is defined first, on the basis of measurement and defective eyesight data of the eye to be corrected, which volume is located within the cornea and whose removal causes the desired correction of defective eyesight. Removal may be effected, for example, by a cut opening to the surface of the cornea, which cut makes the volume accessible and whose creation is also effected by the planning device or the control data, respectively. For the correction to be equal, if possible, with respect night vision and day vision, the volume should cover the pupil of the dark-adapted eye, if possible. Then, boundary surfaces are determined for said volume, which confine the volume. The boundary surfaces are later provided as cut surfaces by the treatment apparatus or its laser device, respectively, so that the volume can be removed, e.g., taken out. For the boundary surfaces, a control dataset is determined, defining target points which are located in the boundary surface and at which a respective optical breakthrough is to be generated by means of laser radiation so as to form the cut surface. The target points are a three-dimensional pattern and are all located in the previously defined boundary surface. The planning device may also be part of the laser device.

As a result of the method or of the activity of the planning device, a control dataset is present which enables automatic control of the laser device such that the cut surfaces isolating the volume in the cornea may then be produced automatically. The planning device and the treatment apparatus equipped with it, respectively, for surgical correction of defective eyesight, as well as the method of providing control data for a treatment apparatus preferably creates the control dataset automatically from the available measurement data and defective-eyesight data. In advantageous embodiments, the surgeon's assistance is not required.

The planning device may be provided as a computer operating under the control of a program. Optionally, the planning device may be part of the treatment apparatus. Thus, a corresponding computer program product including program code which causes the aforementioned method steps is also a solution of the aforementioned problem.

The control dataset is created on the basis of the determined measurement data and defective-eyesight data of the eye. An independent measuring device can acquire these measurement data. Conveniently, however, the treatment apparatus is connected directly to the measuring device. Suitable measuring devices include, for example, an autorefractor, a refractometer, a keratometer, an aberrometer, an OCT, or a wavefront measuring device, or any combination of such devices or measurement instruments.

The eyesight defect may include hyperopia, myopia, presbyopia, astigmatism, mixed astigmatism (astigmatism in which hyperopia is present in one direction and myopia is present in a direction perpendicular to the former), aspherical aberrations and higher-order aberrations.

A direct data transmission connection of the measuring device to the planning device, or to the treatment apparatus equipped with said planning device, which may be used in one variant, has the advantage that the use of false measurement and defective-eyesight data is avoided with maximum certainty. This applies, in particular, if the transfer of the patient from the measuring device(s) to the laser device is effected by means of a positioning device cooperating with the measuring device or with the laser device, respectively, such that the respective devices recognize whether the patient is in the respective position for measurement or for introduction of laser radiation, respectively. Transferring the patient from the measuring device to the laser device simultaneously allows the transmission of measurement or defective-eyesight data to the treatment apparatus.

It is ensured that the planning device always generates the control dataset assigned to the patient and an erroneous use of a wrong control dataset for a patient is virtually impossible.

This aspect is also addressed by a further embodiment of the invention according to which the control dataset is transmitted to the treatment apparatus and, further, operation of the laser device is preferably blocked until a valid control dataset is present at the laser device. In principle, a valid control dataset may be any control dataset suitable for use with the laser device of the treatment apparatus. In addition, however, said validity may also be made subject to the condition that further verifications are performed, e.g., whether a patient's details additionally stored in the control dataset, for example a patient identification number, correspond to other details which were input separately, for example, at the treatment apparatus, as soon as the patient is in the correct position for operation of the laser device.

Transmission may be effected by means of memory chips (e.g. by USB or memory stick), magnetic storage devices (e.g. diskettes), by radio (e.g. WLAN, UMTS, Bluetooth) or by wire connections (e.g. USB, Firewire, RS232, CAN Bus, ethernet, etc.).

In order to generate the isolated volume, the position of the focus of the focused pulsed laser radiation is usually shifted in three dimensions. Therefore, a two-dimensional deflection of the laser radiation, e.g. by scanning mirrors, is usually combined with a simultaneous shift of the focus in the third spatial direction, e.g. by a telescope. Of course, the shift of the focus position is decisive for the accuracy with which the cut surface isolating the volume can be generated. It has turned out to be convenient to use a contact glass to be placed on the eye and fixing the latter. Such a contact glass is also common in the aforementioned laser keratomes used in the fs LASIK method. The contact glass usually also functions to impart a known shape to the anterior surface of the cornea. In the laser keratomes hitherto known, this shape is a plane, i.e. for operation of the laser keratome the eye is pressed flat in the region of the cornea. Since this is relatively inconvenient for the patient, a curved contact glass has already been described for approaches isolating a volume in the cornea. Such a contact glass then imparts a curvature to the anterior surface of the cornea. Of course, the curvature inevitably results in deformation of the cornea of the eye. Said deformation increases as the curvature of the contact surface of the contact glass deviates from the actual curvature of the cornea of the patient's eye. Therefore, in order to be able to work with a standard contact glass curvature, if possible, it is advantageous to take the cornea's deformation, which occurs when applying a curved contact glass, into consideration in the control dataset, so that the free eye, i.e. the eye not deformed by the contact glass, has the desired boundary surface for the defined volume, regardless of the degree of deformation. Therefore, when generating the control dataset which contains the pattern of the target points, it is preferred to take any deformation of the eye's cornea into consideration, which deformation is present during irradiation of the pulsed laser radiation, in particular a deformation due to the aforementioned contact glass.

This approach allows not only the use, if possible, of a standardized contact glass curvature, but at the same time achieves a higher quality in the correction of defective eyesight. Such consideration of the deformation is not required, in fact, in the known laser keratomes, because they press the eye flat at the cornea by the contact glass. There, generating the lamella required for the LASIK operation is effected by simply generating optical breakthroughs in a plane which is parallel to the contact glass.

The generated control dataset can be used directly to control the treatment apparatus. However, it is convenient to give the treating physician a possibility of intervention, allowing him, on the one hand, to verify the control dataset and, on the other hand, to accommodate special cases or special wishes. One possible special wish is, for example, the position of the cut via which the isolated volume is to be removed from the cornea. This is where ophthalmologists often differ in their opinions. However, legal reasons of liability often make it desirable for the physician to have a possibility of intervention. Therefore, it is convenient for the apparatus, as a further embodiment, that the planning device comprises a display device for visual display of the control dataset and an input device for subsequently altering or influencing the control dataset.

Optical systems are generally not perfect. Of course, this also applies to the focusing of the laser radiation into the cornea. For example, warping of the image field may occur here, as a consequence of which focus positions believed to be positioned in a plane are actually not located in a plane, but in a curved surface. In the known laser keratomes, this aspect does not play any role, because producing the cut which exposes the lamella has no effect on the optical quality of the correction. The actual correction is determined exclusively by the volume of the exposed cornea evaporated with the ablation laser. Therefore, there is no interest in an error correction, e.g. with respect to warping of the image field, in the prior art, especially concerning laser keratomes.

Since the volume to be removed is now defined completely by the focusing of the pulsed laser radiation, it is convenient for the planning device, when generating the control dataset, to allow for and, thus, compensate for any optical focus position errors causing a deviation between the predetermined position and the actual position of the target points when focusing the pulsed laser radiation, by considering a pre-offset which depends on the position of the respective target point. Said pre-offset may be determined, for example by the planning device accessing a correction table or correction function which indicates the focus position error as a function of the position of the respective target point. The correction table or function may be uniformly prescribed for the respective type of equipment or may be determined individually for the respective equipment, which is preferred for reasons of precision.

Analog considerations apply to the method according to the invention, wherein optical focus position errors, which cause a deviation between the predetermined position and the actual position of the target points when focusing the pulsed laser radiation, are now offset and compensated for by a pre-offset depending on the position of the respective target point, so as to determine the boundary surface or the three-dimensional pattern of the target points.

The boundary surface isolates the volume if it is provided as a cut surface after using the pulsed laser radiation. Thus, the boundary surface automatically has anterior and posterior sections, with the terms "anterior" and "posterior" herein corresponding to standard medical nomenclature. In principle, it is possible to provide the boundary surface as a free-form surface. However, generating the control dataset is easier if the boundary surface is composed of an anterior partial surface and a posterior partial surface. One of said partial surfaces can then be provided at no constant distance from the surface of the cornea. The other one is then inevitably at a constant distance from the anterior surface of the cornea. The partial surface located at a constant distance from the anterior surface of the cornea, generally the anterior partial surface, is thus usually spherical. This applies exactly if the cornea of the eye is pressed onto a spherical contact glass. The optical correction is then effected by the shape of the other partial surface, usually that of the posterior partial surface. This considerably simplifies the computing effort.

One possibility of indicating the defective-eyesight data consists in determining the refractive power $B_{BR}$ of spectacles suitable for correction of defective eyesight, which have to be arranged at a distance $d_{HS}$ anterior to the corneal vertex so as to achieve the desired correction of defective eyesight. Determining these parameters is a usual standard in ophthalmology and enables the use of wide-spread and long since introduced measuring devices. In order to generate the control dataset, use is simply made of the defective-eyesight data for a conventional correction by spectacles. It goes without saying that such data may also include corrections of astigmatism. A usual formula for the refractive power $B_{BR}$ of spectacles is, for example, the equation (1) given in the following description of the figures. It indicates the spherical refraction error Sph as well as the cylindrical refraction error Cyl wherein, of course, the latter requires that the cylindrical axis θ be known.

For correction of defective eyesight, a volume is removed from the cornea by the treatment apparatus, i.e. using the control datasets generated in the method according to the invention. The ultimate goal is to alter the curvature of the cornea such that a correction of defective eyesight is achieved. A particularly direct, exact and simple calculation of the curvature of the anterior surface of the cornea to be achieved for correction results from the following equation:

$$R_{CV}^*=1/((1/R_{CV})+B_{BR}/((n_c-1)(1-d_{HS}\cdot B_{BR})))+F.$$

In this equation, $R_{CV}^*$ designates the radius of curvature of the anterior surface of the cornea after removal of the volume, $R_{CV}$ designates the radius of curvature of the cornea prior to removing the volume (this radius being included in the measurement data), $n_c$ designates the refractive power of the material of the cornea (generally about 1.376), $d_{HS}$ designates the distance at which spectacles having the aforementioned refractive power must be located anterior to the corneal vertex, and F designates a factor which is a measure for the optical effect of the decrease in the thickness of the cornea on the visual axis due to the distance of the volume. For a simplified calculation, the factor F can be zero. If a more precise calculation is desired, F can be calculated as follows:

$$F=(1-1/n_c)\cdot(d_C^*-d_C),$$

wherein $d_C$ or $d_C^*$, respectively, designates the thickness of the cornea before and after removal of the volume, respectively. The radius $R_{CV}^*$ is then iteratively calculated by deriving the quantity $(d_C^*-d_C)$ during each iteration step from the difference $(R_{CV}^*-R_{CV})$ and applying the corresponding result, thus obtained for the change in thickness, to the calculation of $R_{CV}^*$ in the next iteration step. For example, the iterative calculation is aborted when only a small difference for F occurs between two iterative steps and said difference is smaller than a limit value.

The method of the invention or the treatment apparatus of the invention comprising the planning device operates with particular ease if, as mentioned, the optical correction to be effected by removing said volume is mainly defined by the curvature of a partial surface which is at a non-constant distance from the anterior surface of the cornea and limits the volume. Advantageously, this surface is the posterior partial surface, because this partial surface then has a radius of curvature which equals the above-mentioned radius of curvature minus the constant distance between the anterior partial surface and the anterior surface of the cornea.

The control dataset provides a file enabling fully automatic surgery with respect to the control of the treatment apparatus or to a corresponding operation of the treatment apparatus, respectively. For this purpose, the control dataset provides the laser device with target points onto which the focused laser beam has to be directed when emitting laser pulses. Thus, the focus of the focused laser radiation is then shifted such that follows a path curve over the predetermined target points. In terms of the calculation technique or with respect to the shifting speed, it is particularly favorable if the path curve is a spiral. In the case of the aforementioned anterior or posterior partial surface, one spiral is predetermined for each partial surface. With the focus following a spiral, it is possible to operate the corresponding deflecting device of the treatment apparatus near its maximum frequency, because e.g., when describing a spiral, two galvanometer scanners can be each operated near or at their respective maximum frequencies.

When defining the path, it must be generally ensured that the laser pulses are emitted on said path. The target points will then define nodes or sample points of the path. Although the density at which the target points predetermine the path may correspond to the density at which the points, which receive each a pulse of the laser radiation, are arranged on the path, this is not strictly required. On the contrary, it is even preferred that the target points represent only a subset of those points onto which laser pulses are emitted. On the one hand, the control dataset will then be drastically reduced in terms of its data volume; on the other hand, the calculating effort will be reduced in all those steps where a non-functional description of the path curve in the boundary surface shall or can be worked with, but where the target point coordinates have to be processed individually. An example of this is the aforementioned correction with respect to the curvature of the image field.

Therefore, it is preferred for the apparatus if the laser device shifts the focused laser radiation along a path over a pattern of target points, with pulses of the pulsed laser radiation being emitted into the cornea also at points located on the path and between the target points.

This applies in analogy to the method according to the invention, namely that the control dataset is provided for a laser device which shifts the focused laser radiation along a path over the pattern of target points, wherein the control dataset is generated such that the target points in the pattern represent only a subset of the points onto which the laser device emits the pulsed laser radiation. The control dataset is thus adapted to the shifting speeds of the laser device which are achievable.

As a result, the frequency of the sample points (or nodes) predetermined or applied in the laser device for shifting the focus position differs from that which occurs when generating the laser pulses. Of course, the control dataset per se usually does not contain any indication relating to the frequency, even if this is possible. Due to the maximum shifting speed or the highest signal frequencies applied when shifting the focus of the laser radiation, the definition of the target points naturally corresponds to a path speed or a shifting speed in the respective coordinates used for description. In the preferred embodiment, the spacing between the target points in combination with the path speed and the laser pulse frequency which can be realized by the laser device now has the effect that laser pulses are also emitted automatically at points in time where the focus is still shifted from one target point to the next. This approach has the advantage that, during operation of the treatment apparatus, the target points are/are to be predetermined with a frequency of less than the frequency at which the pulses of the pulsed laser radiation are/are to be emitted into the cornea by the laser device.

It goes without saying that predetermining target points in the control dataset does not mean that the focus has to rest, i.e., that a shifting speed equaling zero has to be present at these target points when the laser pulse is emitted onto the target point. In the sense of quickly producing as the cut surface as the determined boundary surface of the defined volume, it is advantageous if the synchronization of the shift in focus position and the emission of the laser pulses is achieved such that a laser pulse, although emitted under continuous deflection of the focus, still enters the cornea at the target point. Thus, the pulsed laser radiation is applied while continuously shifting the focus position, e.g. in moving scanning mirrors. This feature causes a systematic difference over known shot files for ablation lasers, wherein a shot of the ablation laser is not emitted until the deflection of the laser beam steadily targets a determined point.

INVENTION PART B

The invention relates to a treatment apparatus for surgical correction of defective eyesight in the eye of a patient, which apparatus comprises a laser device controlled by a control device, said laser device separating corneal tissue by irradiation of laser radiation so as to isolate a volume located within the cornea, wherein the control device controls the laser device for focusing the laser radiation into the cornea by providing target points located in the cornea.

The invention further relates to a method of generating control data for a laser device of a treatment apparatus for surgical correction of defective eyesight in the eye of a patient, said laser device separating corneal tissue by irradiation of laser radiation so as to isolate a volume located within the cornea, wherein during operation of the treatment apparatus the control data provide the laser device with target points for the focused laser radiation, said target points being located within the cornea.

Finally, the invention further relates to a method of surgical correction of defective eyesight in the eye of a patient, wherein a volume is isolated in the cornea and, for this purpose, laser radiation is focused on target points arranged in a pattern within the cornea, so as to separate corneal tissue.

Spectacles are the classic means of correction defective eyesight of the human eye. Meanwhile, however, increasing use is made of refractive surgery which causes a correction of defective eyesight by modifying the cornea. Several surgical methods aim to selectively modify the cornea so as to influence light refraction. Different surgical methods are known for this purpose. The most widespread of these is presently the so-called laser in situ keratomileusis, also abbreviated as LASIK. In this method, a corneal lamella (or flap) is first created on one side at the corneal surface and folded aside. Detachment of this lamella can be effected using a mechanical microkeratome or a so-called laser keratome as distributed by Intralase Corp., Irvine, USA, for example. Once the lamella has been created and folded aside, the LASIK operation uses an excimer laser which, by ablation, removes corneal tissue thus exposed. Once a volume of the cornea has been evaporated in this manner, the corneal lamella is folded back to its initial place.

The application of a laser keratome for creating the flap is advantageous, because it will decrease the risk of infection and increase the quality of the cut. In particular, the flap can be produced with a much more constant thickness. Also, the cut is potentially smoother, thus reducing later optical interferences by this boundary surface which remains even after surgery.

When generating a cut surface in the cornea by laser radiation, several processes take place in sequence, initiated by the pulsed laser radiation. If the power density of the radiation exceeds a threshold value during a pulse, an optical breakthrough forms, which produces e.g. a plasma bubble in the cornea. Said plasma bubble grows due to expanding gases after the optical breakthrough has formed. If the optical breakthrough is not maintained, the gas generated in the plasma bubble will be absorbed by the surrounding tissue, and the bubble will disappear again. Tissue-separating effects acting without a plasma bubble are also possible. For the sake of simplicity, all such processes are summarized here by the term "optical breakthrough", i.e., this term is intended to include not only the actual optical breakthrough, but also the effects resulting therefrom in the cornea.

In order to separate tissue, the laser radiation is applied in pulsed form, with the pulse duration usually being less than 1 ps. The required power density of the respective pulse for causing the optical breakthrough is thus generated in a tiny spatial region. In this respect, U.S. Pat. No. 5,984,916 clearly shows that the spatial region of the optical breakthrough (of the interaction produced in this case) depends strongly on the pulse duration. Thus, high focusing of the laser beam in combination with the aforementioned short pulses allows the optical breakthrough to be placed in the cornea with pinpoint accuracy.

To produce a cut, a series of optical breakthroughs are generated at predetermined locations such that a cut surface is generated thereby. In the aforementioned laser keratome, the cut surface forms the lamella to be folded aside prior to the use of laser ablation.

Of course, the precision with which the cut surface is generated is decisive for the optical correction in the end. This applies, in particular, to advanced laser surgery correction methods for defective eyesight, wherein a volume located within the cornea is isolated by a three-dimensional cut surface to make it removable. In contrast to the laser keratome, the position of the cut surface is then directly relevant for optical correction. On the other hand, in the conventional LASIK method, only the precision with which the laser ablation is effected is important for the quality of the optical correction, which can be recognized already by the fact that the generation of the corneal lamella is also possible with a mechanical knife working in a comparatively coarse manner and is or has been practiced also in a great multiplicity of surgeries.

Therefore, it is an object of the invention to provide a treatment apparatus or a method of the aforementioned type such that cut surfaces can be produced with great precision.

The invention acknowledges the fact that optical systems are usually not perfect. An error in focusing the laser radiation in the cornea has an effect on the production of cut surfaces. This applies, in particular, to errors in the focus position due to which focus positions believed to be positioned in a plane are actually not located in a plane, but in a curved surface. In the known laser keratomes, this aspect does not play any role, because producing the cut which exposes the lamella has no meaning for the optical quality of the correction. However, when the volume to be isolated and to be removed is defined completely by the focusing of the pulsed laser radiation, the method according to the invention provides that focus position errors causing a deviation between the predetermined position and the actual position of the target points during focusing of the laser radiation, which is preferably applied in pulsed form, are allowed for by a corresponding pre-offset in the opposite direction.

Said pre-offset causes a pre-distortion of the arrangement of target points such that, in combination with the focus position error, the target points are re-located at the position desired for the use of the treatment apparatus.

The pre-offset may be conveniently determined by a correction table or correction function which indicates the focus position error as a function of the position of the respective target point. This table or function may be uniformly prescribed for the respective type of equipment or, which is preferred for reasons of precision, may be individually determined for the respective equipment, for example by the manufacturer of said equipment or upon installation of the equipment at the user's site.

The optics used to focus the laser radiation can be provided such, with an acceptable effort, that the focus position error is substantially an axial focus position error and rotation-symmetric to the optical axis. For this variant, it is then preferred that each pre-offset shifts the respective target point parallel to the optical axis and that the correction table or function depend only on an axial coordinate and a radial coordinate when the target points are described in cylindrical coordinates. For convenience, the origin of the cylindrical coordinate may be placed at the point where the optical axis passes through the anterior surface of the cornea or through a vertex of any contact glass used.

An analytic definition of the set of target points can be selected when determining the target points. This is particularly easy if a path is defined along which the focus of the laser radiation is to be shifted so as to form the desired cut surface which will isolate the volume. The target points merely need to be selected from among the points of the path. Since the correction with respect to the focus position error will usually not be present as a transcendent, analytic or even linear function, and in most cases only an interpolation by polynomials or splines will be possible at best, it is preferred to select the target points from the path prior to the correction. This approach has the advantage that a simple, low computational effort is necessary to determine the target points.

Simplicity is increased further if the path is determined by one or more functional equation(s) such that the evaluation of said functional equation(s) yields the target points at different nodes. Until then, a transcendent description of the beam deflection is possible, which naturally incurs a very strongly reduced calculating effort than if a large quantity of target points are managed. The actual target coordinates are present only after evaluation of the functional equation(s) at the nodes. They will then represent control data which will be applied during operation of the treatment apparatus. Of course, these control data can be still further processed so as to allow for device-specific adaptations, e.g. determination of corresponding voltage levels for the coordinates, the previously determined amplitude or phase characteristics of galvanometer mirrors, etc.

As already mentioned, the position of the focus of the generally pulsed laser radiation is three-dimensionally shifted in order to produce a cut surface. Therefore, a two-dimensional deflection of the laser radiation, e.g., by galvanometer mirrors, is usually combined with a simultaneous focus shift in the third spatial direction, e.g., by a telescope. Of course, the adjustment of the focus position is decisive for the accuracy with which the cut surface can be generated by the target points. It has turned out to be convenient for this purpose to use a contact glass to be placed on the eye and fixing the latter. Such a contact glass is also common in the aforementioned laser keratomes. The contact glass usually also functions to impart a known shape to the anterior surface of the cornea. In the known laser keratomes, the shape is a plane, i.e. the eye is pressed flat in the region of the cornea. Since this is relatively inconvenient for the patient, a curved contact glass comprising a curved contact surface facing the eye has already been described for approaches isolating a volume in the cornea by laser surgery. Such a contact glass then imparts a curvature to the anterior surface of the cornea. Of course, the curvature inevitably results in deformation of the cornea of the eye. Said deformation increases as the curvature of the contact surface deviates from the actual curvature of the cornea of the patient's eye increases. Therefore, in order to be able to work with a standard contact surface curvature, it is advantageous to take into consideration the deformation of the cornea which occurs when applying a curved contact glass, so that the target points for the free eye, i.e., the eye not deformed by the contact glass, are ultimately located at the desired positions, regardless of the degree of deformation, and thereby a desired boundary surface is ultimately generated for the volume to be removed.

On the one hand, the deformation of the cornea can be taken into account on the basis of the target points, i.e., when the individual coordinates of the target points have been determined. On the other hand, the deformation can also be taken into account by means of a corresponding transformation of the path along which the focus is to be shifted. It is preferred for the treatment apparatus that the control device, when determining the path or the target points, take a deformation of the cornea into consideration, which deformation occurs during irradiation of the pulsed laser radiation, in particular due to a contact glass. Analog features apply to the method according to the invention.

It is particularly favorable in terms of the calculating load, especially for a path given by transcendent functional equations, to first determine the path with respect to the non-deformed eye and then to modify said path so as to compensate for the deformation of the cornea of the eye. In a final step, the path function(s) are evaluated at certain nodes, so as to determine the coordinates for the target points, which are then corrected in a final step, as described, with respect to focus position errors.

Particularly simple computational treatment is obtained if the target points are arranged along paths which extend in a spiral shape. For example, the cut surface to be produced, which isolates the volume, can be divided into two partial surfaces or sub-surfaces, an anterior partial surface and a posterior partial surface. The sub-surfaces can be respectively formed by shifting the focus along a spiral-shaped path.

The method according to the invention for preparing the control data can also be effected without human assistance. In particular, it may be performed by a computer which determines from corresponding data, e.g., from the functionally defined path curves, the control data by selecting the nodes matching the shifting speed of the laser device which represents the target system of the control data. In particular, determining the control data does not require any assistance from a physician, because said determination of the control data does not yet involve any therapeutic intervention. Such intervention will take place only upon application of the previously determined control data.

INVENTION PART C

The invention relates to a treatment apparatus for surgical correction of defective eyesight in the eye of a patient, said apparatus comprising a laser device which is controlled by a control device and which separates corneal tissue by irradiation of laser radiation, wherein the control device controls the laser device to focus the laser radiation into the cornea at target points arranged in a pattern within the cornea and selects the pattern such that a volume is thereby isolated in the cornea, with the removal of said volume from the cornea causing the desired correction of defective eyesight.

The invention further relates to a method of generating control data for a laser device of a treatment apparatus for surgical correction of defective eyesight in the eye of a patient, which laser device separates corneal tissue by irradiation of focused laser radiation, wherein the control data provide the laser device with target points for the focused laser radiation during operation of the treatment apparatus, which target points are arranged in a pattern within the cornea such that a volume is thereby isolated in the cornea, with the removal of said volume from the cornea causing the desired correction of defective eyesight.

Finally, the invention relates to a method for surgical correction of defective eyesight in an eye of a patient, wherein, in order to separate corneal tissue, laser radiation is focused onto target points arranged in a pattern within the cornea and, thereby, a volume is isolated in the cornea, with the removal of said volume causing the desired correction of defective eyesight.

Spectacles are the classic means of correction defective eyesight of the human eye. Meanwhile, however, increasing use is made of refractive surgery which causes a correction of defective eyesight by modifying the cornea. Said surgical methods aim to selectively modify the cornea so as to influence light refraction. Several surgical methods are known for this purpose. The most widespread of these is presently the so-called laser in situ keratomileusis, also abbreviated as LASIK. In this method, a corneal lamella (or flap) is first created on one side at the corneal surface and folded aside. Detachment of this lamella can be effected using a mechanical microkeratome or a so-called laser keratome as distributed by Intralase Corp., Irvine, USA, for example. Once the lamella has been created and folded aside, the LASIK operation uses an excimer laser which, by ablation, removes corneal tissue thus exposed. Once a volume of the cornea has been evaporated in this manner, the corneal lamella is folded back to its initial place.

The application of a laser keratome for creating the flap is advantageous, because it will decrease the risk of infection and increase the quality of the cut. In particular, the flap can be produced with a much more constant thickness. Also, the cut is potentially smoother, thus reducing later optical interferences by this boundary surface which remains even after surgery.

When generating a cut surface in the cornea by laser radiation, several processes take place in sequence, initiated by the pulsed laser radiation. If the power density of the radiation exceeds a threshold value during a pulse, an optical breakthrough forms, which produce, e.g., a plasma bubble in the cornea. Said plasma bubble grows due to expanding gases after the optical breakthrough has formed. If the optical breakthrough is not maintained, the gas generated in the plasma bubble will be absorbed by the surrounding tissue, and the bubble will disappear again. Tissue-separating effects acting without a plasma bubble are also possible. For the sake of simplicity, all such processes are summarized here by the term "optical breakthrough", i.e., this term is intended to include not only the actual optical breakthrough, but also the effects resulting therefrom in the cornea.

In order to separate tissue, the laser radiation is applied in pulsed form, with the pulse duration usually being less than 1 ps. The required power density of the respective pulse for causing the optical breakthrough is thus generated in a tiny spatial region. In this respect, U.S. Pat. No. 5,984,916 clearly shows that the spatial region of the optical breakthrough (of the interaction produced in this case) depends strongly on the pulse duration. Thus, high focusing of the laser beam in combination with the aforementioned short pulses allows the optical breakthrough to be placed in the cornea with pinpoint accuracy.

To produce a cut, a series of optical breakthroughs are generated at predetermined locations such that a cut surface is generated thereby. In the aforementioned laser keratome, the cut surface forms the lamella to be folded aside prior to the use of laser ablation.

In the conventional LASIK method, exposed corneal tissue is evaporated, which is also referred to as "abrading" the cornea by means of laser radiation. The volume removal required for a correction of defective eyesight is then performed for each surface element of the exposed cornea by the number of laser pulses and their energy. Therefore, in the LASIK method a so-called shot file is provided for the ablation laser, which file predetermines for various points on the cornea of the eye how often laser beam pulses are to be directed on defined points on the cornea and with what energy. In doing so, the volume removal was heuristically determined, not least because it depends largely on the ablation effect of the laser beam and, thus, on the wavelength, the fluence, etc. of the radiation employed. The condition of the eye's cornea also plays a role; here, the moisture content of the eye's cornea is to be mentioned.

Now, values gained by experience, which are suitable for abrading the cornea by means of ablation laser radiation, cannot be used for improved methods of refractive eye surgery, wherein the volume to be removed from the cornea is not removed by ablation of exposed corneal tissue, but is isolated by a three-dimensional cut surface in the cornea and is thus made removable.

Therefore, it is an object of the present invention to provide a treatment apparatus or method of the above-mentioned type such that the cut surface can be precisely defined.

According to the invention, this object is achieved by a treatment apparatus of the above-mentioned type, wherein the cornea reduced by said volume has a radius of curvature $R_{CV}^*$ which satisfies the following equation:

$$R_{CV}^*=1/((1/R_{CV})+B_{BR}/((n_c-1)(1-d_{HS} \cdot B_{BR})))+F,$$

wherein $R_{CV}$ is the radius of curvature of the cornea prior to removal of said volume, $n_c$ is the refractive power of the material of the cornea, F is a correction factor, $B_{BR}$ is the refractive power of spectacles suitable to effect the correction of defective eyesight, and $d_{HS}$ is the distance at which said spectacles having the refractive power $B_{BR}$ would have to be located anterior of the corneal vertex in order to achieve the desired correction of defective eyesight by means of the spectacles.

According to the invention, this object is further achieved by a method for generating control data for a laser device of the above-mentioned type, wherein in the method for generating control data for a laser device of a treatment apparatus for surgical correction of defective eyesight in a patient's eye, which laser device separates corneal tissue by irradiation of focused laser radiation, control data provide the laser device with target points for the focused laser radiation during operation of the treatment apparatus, which target points are arranged in a pattern within the cornea such that a volume is thereby isolated in the cornea, with removal of said volume from the cornea causing the desired correction of defective eyesight.

Finally, the object is also achieved by a method for surgical correction of defective eyesight as mentioned above, wherein the cornea reduced by said volume assumes a radius of curvature $R_{CV}^*$ which satisfies the following equation:

$$R_{CV}^*=1/((1/R_{CV})+B_{BR}/((n_c-1)(1-d_{HS} \cdot B_{BR})))+F,$$

wherein $R_{CV}$ is the radius of curvature of the cornea prior to removal of said volume, $n_c$ is the refractive power of the material of the cornea, F is a corrective factor, $B_{BR}$ is the refractive power of spectacles suitable to effect the correction of defective eyesight, and $d_{HS}$ is the distance at which the spectacles having the refractive power $B_{BR}$ would have to be located anterior of the corneal vertex in order to achieve the desired correction of defective eyesight by means of the spectacles.

Thus, the invention provides a control value or a calculation parameter, on the basis of which the volume to be removed and, thus, the cut surface isolating said volume in the cornea can be calculated as exactly as possible. The invention defines an equation for the radius of curvature which the cornea has after removal of the volume isolated by the treatment apparatus or the method, respectively. This equation allows the volume to be calculated in an analytically exact manner. The heuristic approach, as applied when abrading the cornea exposed in the LASIK process, is replaced by an analytic description of the anterior surface of the cornea, as it has to be present after correction, which enables precise calculation of the volume to be removed in the improved ophthalmic surgical method.

The description of the curvature of the anterior corneal surface after correction is based on defective-eyesight data indicating the refractive power $B_{BR}$ of spectacles suitable for the correction of defective eyesight, which spectacles have to be located at a distance $d_{HS}$ anterior to the corneal vertex in order to achieve the desired correction of defective eyesight. Determining these parameters is a usual standard in ophthalmology and enables the use of wide-spread and long since introduced measuring devices. Thus, when calculating the volume to be isolated in the cornea, defective-eyesight data for a conventional correction by spectacles are to be used.

Of course, such data can also include astigmatism corrections or even corrections of higher orders of aberration. A usual formula for the refractive power $B_{BR}$ of spectacles is, for example, the equation (1) given in the following description of the Figures. It indicates the spherical refraction error Sph as well as the cylindrical refraction error Cyl and, of course, the latter requires knowledge of its cylindrical axis θ.

The correction factor F is a measure of the optical effect of the reduction in the thickness of the eye's cornea on the visual axis due to removal of said volume. In a simplified calculation, the factor F can be set to zero. If a more precise calculation is desired, F can be calculated as follows:

$$F=(1-1/n_c)\cdot(d_C^*-d_C),$$

wherein $d_C$ and $d_C^*$ respectively refer to the thickness of the cornea before and after removal of said volume, and the radius $R_{CV}^*$ is iteratively calculated, by deriving a change in thickness $(d_C^* - d_C)$ from the difference $(R_{CV}^* - R_{CV})$ in each iteration step and applying the corresponding result, thus obtained for the change in thickness, to the calculation of $R_{CV}^*$ in the next iteration step. For example, the iterative calculation of F is aborted when only a difference for F occurs between two iterative steps which are smaller than a limit value.

Taking into consideration a cylindrical eyesight defect, the radius which the cornea has after reduction by said volume, naturally is a function of the cylindrical angle, i.e., of an angle perpendicular to the visual axis, as is common in ophthalmology to describe an astigmatic eyesight defect. Of course, the same applies for the refractive power of spectacles on which the equation for the radius is based.

Now, according to the invention, the volume is determined or determinable such that the cornea has the defined radius of curvature after removal of said volume. A definition of the volume which is particularly easy to calculate and, above all, also easy to realize limits the volume by a boundary surface which is divided into an anterior and a posterior partial surface, with the anterior partial surface being located at a constant distance $d_F$ from the anterior corneal surface. The terms "anterior" and "posterior" correspond to standard medical nomenclature.

Due to the anterior partial surface located at a constant distance from the corneal surface, this partial surface is particularly easy to generate. Of course, the posterior partial surface will then inevitably have no constant distance from the anterior corneal surface. Optical correction is effected by the shape given to the posterior partial surface. This approach considerably reduces the calculating effort, because a spherical partial surface (the anterior partial surface) is particularly easy to calculate, and the calculating effort is concentrated on determining the posterior partial surface.

It has turned out, in a surprising manner, that such an approach enables a simple analytic description of the posterior partial surface at the same time. This is because said surface has a curvature which can be identical, except for an additive constant, with the curvature of the anterior corneal surface after removal of said volume. Said constant incorporates the distance which the anterior partial surface is posterior of the anterior corneal surface.

In particular, this embodiment allows the posterior partial surface to be described with particular ease by cylindrical coordinates whose origin is located at the point where the visual axis intersects the anterior corneal surface, namely by the equation:

$$z_L(r,\varphi)=R_L(\varphi)-(R_L^2(\varphi)-r^2)^{1/2}+d_L+d_F$$

wherein $d_L$ sets a minimum thickness of the volume to be removed.

The minimum thickness $d_L$, which is optional, assists the subsequent removal of the isolated volume, because said volume then has a certain minimum thickness (e.g. at its periphery), namely the value $d_L$. At the same time, it can thus be ensured that the volume fully covers the pupil of the eye, preferably even when the eye is dark-adapted. This ensures that the optical correction is optimal for all visual conditions encountered by the patient.

The method according to the invention for preparing the control data can be effected without human assistance. In particular, it may be performed by a computer which determines from corresponding data, e.g., from the functionally defined path curves, the control data by effecting the selection of the sample points or nodes in a manner matching the shifting speed of the laser device representing the target system for application of the control data. In particular, determining the control data does not require any assistance from a physician, because said determination of the control data does not yet involve a therapeutic intervention. Such intervention will take place only upon application of the previously determined control data.

INVENTION PART D

The invention relates to a treatment apparatus for surgical correction of defective eyesight in a patient's eye, said apparatus comprising a laser device which separates corneal tissue by irradiation of pulsed laser radiation, said laser radiation being focused on target points arranged in a pattern within the cornea.

The invention further relates to a method for generating control data for a laser device of a treatment apparatus for surgical correction of defective eyesight in a patient's eye, which laser device separates corneal tissue by irradiation of focused, pulsed laser radiation having a specific pulse frequency, wherein the laser device is provided with target points for the pulsed laser radiation which are arranged in a pattern within the cornea.

Further, the invention relates to a method for surgical correction of defective eyesight in a patient's eye, wherein pulsed laser radiation is focused on target points, arranged in a pattern within the cornea, so as to separate corneal tissue.

Spectacles are the classic means of correction defective eyesight of the human eye. Meanwhile, however, increasing use is made of refractive surgery which causes a correction of defective eyesight by modifying the cornea. Said surgical methods aim to selectively modify the cornea so as to influence light refraction. Several surgical methods are known for this purpose. The most widespread of these is presently the so-called laser in situ keratomileusis, also abbreviated as LASIK. In this method, a corneal lamella (or flap) is first created on one side at the corneal surface and folded aside. Detachment of this lamella can be effected using a mechanical microkeratome or a so-called laser keratome as distributed by Intralase Corp., Irvine, USA, for example. Once the lamella has been created and folded aside, the LASIK operation uses an excimer laser which, by ablation, removes corneal tissue thus exposed. Once a volume of the cornea has been evaporated in this manner, the corneal lamella is folded back to its initial place.

The application of a laser keratome for creating the flap is advantageous, because it will decrease the risk of infection and increase the quality of the cut. In particular, the flap can be produced with a much more constant thickness. Also, the cut is potentially smoother, thus reducing later optical interferences by this boundary surface which remains even after surgery.

When generating a cut surface in the cornea by laser radiation, several processes take place in sequence, initiated by the pulsed laser radiation. If the power density of the radiation exceeds a threshold value during a pulse, an optical breakthrough forms, which produces e.g. a plasma bubble in the cornea. Said plasma bubble grows due to expanding gases after the optical breakthrough has formed. If the optical breakthrough is not maintained, the gas generated in the plasma bubble will be absorbed by the surrounding tissue, and the bubble will disappear again. Tissue-separating effects acting without a plasma bubble are also possible. For the sake of simplicity, all such processes are summarized here by the term "optical breakthrough", i.e., this term is intended to include not only the actual optical breakthrough, but also the effects resulting therefrom in the cornea.

In order to separate tissue, the laser radiation is applied in pulsed form, with the pulse duration usually being less than 1 ps. The required power density of the respective pulse for causing the optical breakthrough is thus generated in a tiny spatial region. In this respect, U.S. Pat. No. 5,984,916 clearly shows that the spatial region of the optical breakthrough (of the interaction produced in this case) depends strongly on the pulse duration. Thus, high focusing of the laser beam in combination with the aforementioned short pulses allows the optical breakthrough to be placed in the cornea with pinpoint accuracy.

To produce a cut, a series of optical breakthroughs are generated at predetermined locations such that a cut surface is generated thereby. In the aforementioned laser keratome, the cut surface forms the lamella to be folded aside prior to the use of laser ablation.

Obviously, the cut surface is to be generated as quickly as possible, of course. Therefore, a pulse frequency of the laser which is as high as possible is desired. Naturally, this also increases the control effort accordingly.

This applies, in particular, if advanced applications of refractive surgery are desired, wherein the volume to be removed from the cornea is not removed by ablation of exposed corneal tissue, but by creating a three-dimensional cut surface which encloses the volume to be removed. Such applications involve not only more complex cut shapes, but also require processing of a considerably larger cut surface.

Therefore, it is the object of the present invention to provide an apparatus of the above-mentioned type or a corresponding method, respectively, by which a cut surface can be produced with little effort and as quickly as possible.

According to the invention, this object is achieved by a treatment apparatus of the above-mentioned type, wherein the laser device shifts the focused laser radiation along a path via the pattern of target points and emits pulses of the pulsed laser radiation into the cornea even at points which are located on the path between the target points.

The object is further achieved by a method of generating control data of the above-mentioned type, wherein the control data define the target points as points of a path along which the focus of the laser radiation is to be shifted during the intended operation of the treatment apparatus, with the target points being spaced apart on the path such that, during operation of the treatment apparatus, pulses of the pulsed laser radiation are also emitted into the cornea at points located on the path between the target points, due to the focus shifting speed and the pulse frequency of the laser device.

Finally, the object is also achieved by a method for surgical correction of defective eyesight as mentioned above, wherein the focused laser radiation is shifted along a path via the pattern of the target points and pulses of the pulsed laser radiation are emitted into the cornea also at points located on the path between the target points.

Thus, the invention no longer provides one target coordinate exactly for each laser pulse. Instead, target points are provided at a greater distance than that at which the laser pulses are located in the cornea. Thus, laser pulses which were emitted into the cornea while shifting the focus position from one target point to the next are located between the laser pulses for which a target point was provided.

This concept has the advantage that the control requirements for the focus shifting device, which usually performs a three-dimensional focus shift (because the cut surfaces can be assumed to be three-dimensional), are drastically reduced.

If a continuous beam deflection is provided for at the same time, a very quick production of cut surfaces is achieved in addition. In contrast to conventional excimer lasers, there is no need to wait, for each laser pulse, until the focus shifting device has been set to the coordinates of the currently next target point. Rather, a continuously adjusting focus shifting device can be employed. This is particularly advantageous if the cut surfaces are constituted by path curves having a spiral shape. If conventional galvanometer scanning mirrors are then used in the focus shifting device, these can be controlled with oscillations near the scanner's limit frequency, thereby increasing the deflection speed to the maximum technically feasible level.

However, in addition to a simpler control and quicker constitution of the cut surface, respectively, the invention also results in surprising simplifications when generating the target coordinates.

In this respect, it is particularly advantageous if the paths on which the later target points will be located are described, if possible, in the form of functional equations. Having finally defined the path curves, the target points will then be generated by suitable evaluations of the functional equation at nodes which are spaced apart from each other by a selectable amount.

Isolating a volume by a three-dimensional cut surface and making it removable naturally requires datasets which are considerably larger than the datasets of conventional shot files of excimer lasers. On the one hand, this is due to the fact that the third space coordinate, namely the z coordinate, now has to be specified, too. In contrast thereto, in ablation by means of laser radiation, there is always an interaction taking place only on the material surface, so that no z coordinate has to be specified. As a consequence, three-dimensional specifications are required now instead of two-dimensional coordinate sets, thus inevitably increasing the size of the control datasets. Moreover, it is now required to process comparatively larger surfaces than those that were required in conventional laser ablation. This increases the size of the control datasets additionally.

The inventive approach of no longer providing an explicit target coordinate for each point where a laser beam pulse is to be introduced into the cornea helps to drastically reduce the dataset. For example, for a pulse frequency of the pulsed laser radiation of between 50 and 300 kHz, the node frequency may be $\frac{1}{5}$ to $\frac{1}{50}$ of the laser pulse frequency. Of course, the volume of the dataset is also reduced by the corresponding factor. This drastically reduces the transmission overhead as well as the calculating effort for determining the target points and generating the control dataset.

This advantage is particularly noticeable if the path curves, on which are located the points onto which the laser radiation pulses are emitted, are treated, as long as possible, in the form of functional descriptions. In the case of an adroit selection of algorithms, an explicit calculation of target coordinates, i.e., the functional evaluation of the path curve function, is required only if a focus position error has to be corrected, because it usually cannot be described in analytic, functional terms and usually can be described, at best, by interpolation methods, such as polynomial interpolation or spline interpolation. Therefore, it is preferred to functionally describe the path curves and to effect an evaluation of the functional equations for calculation of the target point coordinates only in case of and, if possible, directly before a compensation of a focus position error.

Of course, when providing the nodes, the apparatus parameters of the focus shifting device have to be taken into consideration. Care is taken, of course, that the distance between the target points and the frequency with which these target points are provided are selected such that they can be affected with the shifting speeds of the focus shifting device. However, this is easy to do for the person skilled in the art when adapting the control dataset to a current treatment apparatus.

The method according to the invention for preparing the control data can be effected without human assistance. In particular, it may be performed by a computer which determines from corresponding data, e.g., from the functionally defined path curves, the control data by selecting the nodes so as to match the shifting speed of the laser device representing the target system for application of the control data. In particular, determining the control data does not require any assistance from a physician, because said determination of the control data does not yet involve a therapeutic intervention. Such intervention will take place only when applying the previously determined control data.

BRIEF DESCRIPTION OF THE DRAWINGS

Subject matter hereof may be more completely understood in consideration of the following detailed description of various embodiments in connection with the accompanying figures, in which:

FIG. 1 shows a schematic view of a treatment apparatus or instrument for correction of defective eyesight, FIG. 2 shows a schematic diagram relating to the introduction of pulsed laser radiation into the eye for the correction of defective eyesight by the treatment apparatus of FIG. 1, FIG. 3 shows a further schematic representation of the treatment apparatus of FIG. 1, FIG. 5 shows a schematic sectional view through the eye's cornea and also represents a volume to be removed for correction of defective eyesight, FIG. 6 shows a section through the eye's cornea after removal of the volume of FIG. 5, FIG. 7 shows a sectional view similar to that of FIG. 5;

Figure 1A:
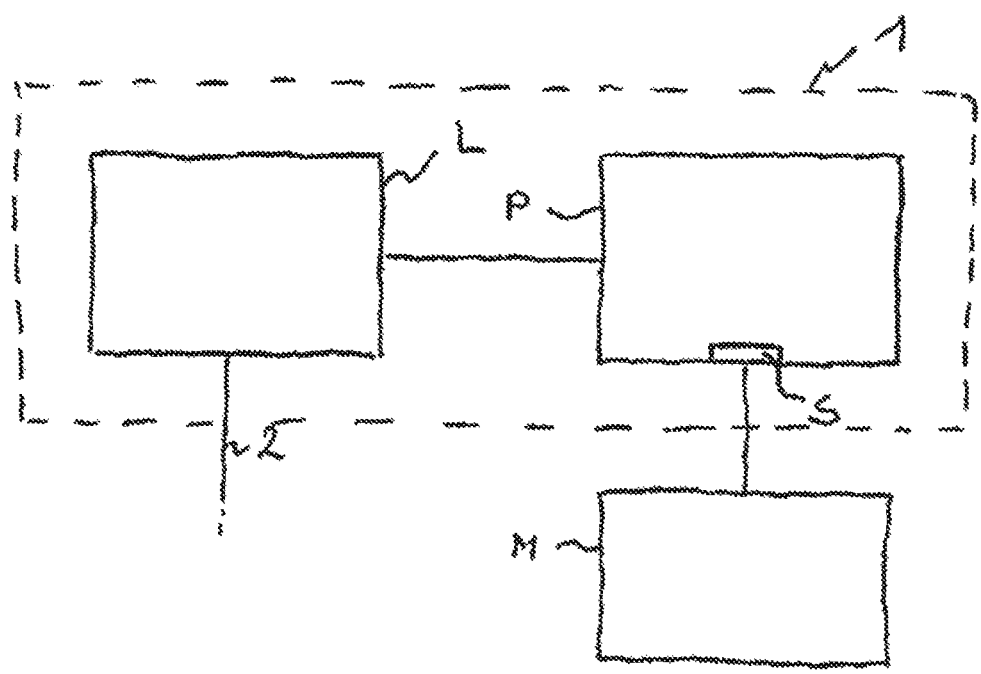
FIG. 1a shows a schematic view with respect to the construction of the treatment instrument of FIG. 1.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

FIG. 1 shows a treatment apparatus 1 for an ophthalmic method similar to those described in EP 1159986 A1 and U.S. Pat. No. 5,549,632. The treatment apparatus 1 causes a correction of defective eyesight at an eye 3 of a patient 4 by means of treatment laser radiation 2. The eyesight defect may include hyperopia, myopia, presbyopia, astigmatism, mixed astigmatism (astigmatism in which hyperopia is present in one direction and myopia is present in a direction perpendicular to the former), aspherical aberrations and higher-order aberrations. In the described embodiments, the treatment laser radiation 2 is applied as a pulsed laser beam focused into the eye 3. The pulse duration is e.g. in the femtosecond range, and the laser radiation 2 acts by means of non-linear optical effects in the cornea. For example, the laser beam comprises short laser pulses of 50 to 800 fs (preferably 100-400 fs) with a pulse repetition rate of between 10 and 500 kHz. In the described exemplary embodiment, the components of the apparatus 1 are controlled by an integrated control unit, which alternatively may be provided separately, of course.

Prior to using the treatment apparatus, the eyesight defect of the eye 3 is measured by one or more measuring devices.

FIG. 1a schematically shows the treatment apparatus 1. In this variant, it comprises at least two devices or modules. A laser device L emits the laser beam 2 onto the eye 3. Operation of the laser device L is fully automatic, i.e., upon a corresponding start signal, the laser device L starts deflection of the laser beam 2 and, thus, generates cut surfaces, which are composed in a manner yet to be described and which isolate a volume in the eye's cornea. The laser device L receives, via control lines not designated in detail, the control data required for operation in advance from a planning device P in the form of a control dataset. Transmission is done prior to operation of the laser device L. Of course, communication may also be wireless. As an alternative to a direct communication, it is also possible to arrange the planning device P spatially separate from the laser device L and to provide a corresponding data transmission channel.

The control dataset is preferably transmitted to the treatment apparatus 1 and, further, operation of the laser device L is preferably blocked until a valid control dataset is present at the laser device L. A valid control dataset may be any control dataset which is basically suitable for use with the laser device L of the treatment apparatus 1. In addition, validity may also be made subject to the condition that further tests are passed, e.g., whether additional details stored in the control data set in respect of the treatment apparatus 1, e.g., an apparatus serial number, or in respect of the patient, e.g., a patient identification number, correspond to other details, e.g., read out at the treatment apparatus or input separately, as soon as the patient is in the correct position for operation of the laser device L.

The planning unit P generates the control dataset which is provided to the laser unit L to perform the surgical operation, said dataset consisting of measurement data and defective-eyesight data determined for the eye to be treated. They are supplied to the planning unit P via an interface S and, in the exemplary embodiment shown, originate from a measuring device M, which previously measured the eye of the patient 4. Of course, the measuring unit M may transmit the corresponding measurement data and defective-eyesight data to the planning device P in any suitable way.

Data transmissions may be effected by means of memory chips (e.g. by USB or memory stick), magnetic storage devices (e.g. diskettes), by radio connections (e.g. WLAN, UMTS, Bluetooth) or by wire connections (e.g. USB, Firewire, RS232, CAN Bus, ethernet, etc.). Of course, the same applies with respect to the data transmissions between the planning device P and the laser device L.

A direct connection of the measuring device M to the treatment apparatus 1, with respect to the data transmissions which may be used in one variant, has the advantage that the use of false measurement and defective-eyesight data is avoided with maximum certainty. This applies, in particular, if the transfer of the patient from the measuring device M or the measuring devices, respectively, to the laser device L is effected by means of a positioning device (not shown in the FIG.) cooperating with the measuring device M or with the laser device L, respectively, such that the respective devices recognize whether the patient 4 is in the respective position for measurement or for introduction of laser radiation 2, respectively. Transferring the patient 4 from the measuring device M to the laser device L may simultaneously allow also the transmission of measurement or defective-eyesight data to the treatment apparatus 1.

Preferably, suitable means ensure that the planning device P always generates the control dataset assigned to the patient 4 and any erroneous use of a wrong control dataset for a patient 4 is virtually impossible.

The efforts of the laser beam 2 are schematically indicated in FIG. 2. The treatment laser beam 2 is focused into the cornea 5 of the eye 6 by optics not designated in detail. This forms in the cornea 5 a focus which covers a spot 6 and in which the power density of the laser radiation is so high that, in combination with the pulse duration, a non-linear effect occurs in the eye. For example, each pulse of the pulsed laser radiation 2 may generate an optical breakthrough in the eye's cornea 5, which breakthrough in turn initiates a plasma bubble schematically indicated in FIG. 2. Thereby, tissue is separated in the cornea 5 by means of this laser pulse. When a plasma bubble forms, the separation of tissue layers covers an area greater than the spot 6 which the focus of the laser radiation 2 covers, although the conditions for generating the breakthrough are achieved only in the focus. For each laser pulse to generate an optical breakthrough, the energy density, i.e., the fluence of the laser radiation, has to be above a certain pulse duration-dependent threshold value. This interrelationship is known to the person skilled in the art, for example, from DE 69500997 T2.

Alternatively, a tissue-separating effect by the pulsed laser radiation can also be produced by emitting several laser radiation pulses within one region, with the spots 6 of several laser radiation pulses overlapping. In this case, several laser radiation pulses will then cooperate to achieve a tissue-separating effect.

However, the type of tissue separation which the treatment apparatus 1 employs is of no further relevance to the following description. It is only essential that pulsed treatment laser radiation 2 is used for this purpose. For example, use can be made of a treatment apparatus 1 as described in WO 2004/032810 A2. Further, it is essential that a multiplicity of laser pulse foci form a cut surface in the tissue, the shape of said cut surface depending on the pattern in which the laser pulse foci are/will be arranged in the tissue. The pattern determines target points for the focus position at which one or more laser pulse(s) is (are) emitted and defines the shape and location of the cut surface. The pattern of the target points is of relevance to the methods and apparatuses explained hereinafter and will be described in more detail.

Now, in order to carry out correction of defective eyesight, material is removed by means of the pulsed laser radiation from an area within the cornea 5 by separating tissue layers which isolate the material and, thus, enable material removal. The material removal causes a change in volume in the cornea, which leads to a change in the optical imaging effect of the cornea 5. This change is dimensioned precisely such that the eyesight defect previously determined is/will be corrected thereby, if possible. In order to isolate the volume to be removed, the focus of the laser radiation 2 is directed at target points in the cornea 5, usually in a region located below the epithelium and Bowman's membrane as well as above Decemet's membrane and the endothelium. For this purpose, the treatment apparatus 1 comprises a mechanism for adjusting the position of the focus of the laser radiation 2 within the cornea 5. This is schematically shown in FIG. 3.

In FIG. 3, elements of the treatment apparatus 1 are indicated only insofar as they are required for understanding the focus adjustment. As already mentioned, the laser radiation 2 is collimated in a focus 7 in the cornea 5, and the position of the focus 7 in the cornea is shifted such that energy from laser radiation pulses is focused into the tissue of the cornea 5 at several locations to produce the cut surface. The laser radiation 2 is provided as pulsed radiation by a laser 8. An xy-scanner 9, which is realized in one variant by two galvanometer mirrors with substantially orthogonal deflections, two-dimensionally deflects the laser beam coming from the laser 8, so that a deflected laser beam 10 is present posterior to the xy-scanner 9. Thus, the xy-scanner 9 causes shifting of the position of the focus 7 in a direction substantially perpendicular to the main direction of incidence of the laser radiation 2 into the cornea 5. For adjustment of the depth position, a z scanner 11 is provided in addition to the xy-scanner 9, which z scanner 11 is provided, for example, as an adjustable telescope. The z scanner 11 ensures that the z position of the location of the focus 7, i.e. its position on the optical axis of incidence, is changed. The z scanner 11 may be arranged preceding or following the xy-scanner 9. Thus, the coordinates referred to hereinafter as x, y, z relate to the shift of the location of the focus 7.

The assignment of the individual coordinates to the spatial directions is not essential for the operative principle of the treatment apparatus 1, but for the sake of simpler description z hereinafter always refers to the coordinate along the optical axis of incidence of the laser radiation 2, and x as well as y designate two mutually orthogonal coordinates in a plane perpendicular to the direction of incidence of the laser beam. The person skilled in the art is certainly aware that a three-dimensional description of the position of the focus 7 in the cornea 5 can also be effected by other coordinate systems; in particular the coordinate system is not required to be orthogonal. Thus, it is not mandatory that the xy-scanner 9 deflects at mutually orthogonal axes; rather, any scanner may be used which is able to shift the focus 7 in a plane in which the axis of incidence of the optical radiation is not located. Thus, non-orthogonal coordinate systems are also possible.

Further, non-straight coordinate systems can also be used to describe or control the location of the focus 7, as will also be explained hereinafter. Examples of such coordinate systems are spherical coordinates as well as cylindrical coordinates.

In order to control the location of the focus 7, the xy-scanner 9 as well as the z scanner 11, which jointly realize a specific example of a three-dimensional focus shifting device, are controlled by a control device 12 via lines not designated in detail. The same applies to the laser 8. The control device 3 provides a suitably synchronous operation of the laser 8 as well as of the three-dimensional focus shifting device, realized by way of example using the xy-scanner 9 as well as the z scanner 11, so that the location of the focus 7 in the cornea 5 is shifted such that, in the end, a material of a determined volume is isolated, with the subsequent removal of the volume causing a desired correction of defective eyesight.

The control device 12 operates on the basis of predetermined control data which prescribe the target points for the focus adjustment. The control data are usually grouped to form a control dataset. According to one embodiment, said control dataset prescribes the coordinates of the target points as a pattern, with the sequence of the target points in the control dataset determining the serial arrangement of the focus locations and, thus, ultimately determining a path curve (also briefly referred to herein as path). In one embodiment, the control dataset contains the target points as more specific control values for the focus location shifting mechanism, e.g., for the xy-scanner 9 and the z scanner 11. For preparation of the ophthalmic method, i.e. before the actual surgical method can be executed, the target points and preferably also their sequence in the pattern are determined. Prior planning of the surgical operation has to be effected by determining the control data for the treatment apparatus 1 whose application will then result in optimal correction of defective eyesight for the patient 4.

Figure 4:
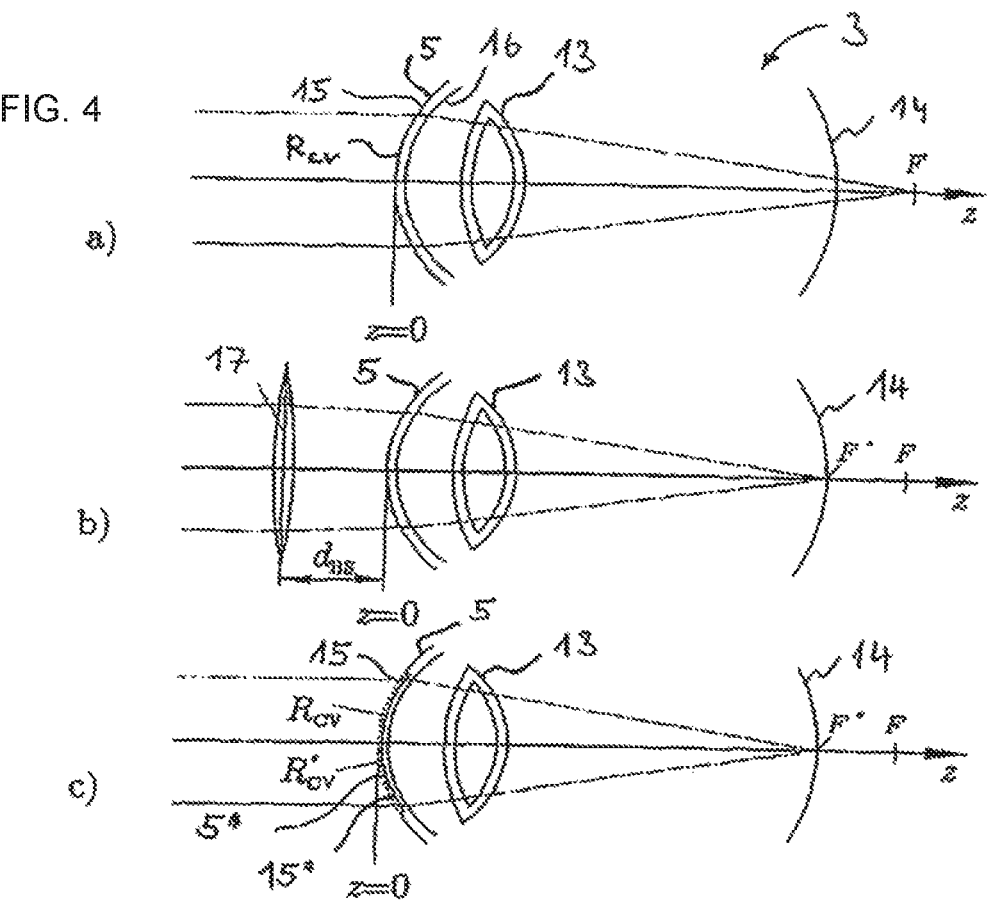
FIG. 4 shows in partial Figures (a), (b) and (c) schematic sectional views illustrating the need for correction at the human eye in case of defective eyesight.

First, the volume to be isolated and to be subsequently removed from the cornea 5 has to be determined. As already described with reference to FIG. 1a, this requires determination of the need for correction. FIG. 4 shows, in partial FIGS. a), b) and c), the optical conditions at the eye 3 of the patient 4. Without a correction of defective eyesight, the situation shown in partial FIG. a) may be present. Together with the eyelens 13, the cornea 5 causes focusing of an object, located at infinity, in a focus F which is located on the z axis behind the retina 14. The imaging effect results, on the one hand, from the eyelens 13, which is relaxed in the non-accommodated eye, as well as, on the other hand, from the eye's cornea 5, which is defined substantially by an anterior corneal surface 15 as well as by a posterior corneal surface 16 and, due to its curvature, also has an imaging effect. The optical effect of the cornea 5 is due to the radius of curvature $R_{CV}$ of the anterior corneal surface. Partial FIG. a) shows the eyesight defect only by way of example; in reality, the above-mentioned, more complex eyesight defects may be present. However, the following description also applies to them, but some of the indicated equations may then include an additional angular dependence, even if it is not explicitly mentioned.

For correction of defective eyesight, an ancillary lens 17 in the form of spectacles is placed in front of the eye 3, in a known manner and as shown in partial FIG. b) of FIG. 4, at a distance $d_{HS}$ from the vertex of the cornea 5. The lens 17 of the spectacles is adapted such, in terms of its refractive power $B_{BR}$, that it shifts the far point of the entire system, i.e., of the eye with the spectacles, from the focal point F to the focal point F*, which is located on the retina 14.

With respect to the nomenclature used in this description, it should be noted that quantities having an asterisk added are quantities obtained after a correction. Accordingly, the focus F* is that focus which is present after the optical correction achieved by the lens 17 of the spectacles in the partial FIG. b) of FIG. 4.

Based on the justified assumption that a change in the thickness of the cornea 5 mainly modifies the radius of curvature of the anterior corneal surface 5 facing the air, but not the radius of curvature of the posterior corneal surface 16 facing the interior of the eye, the radius of curvature $R_{CV}$ of the anterior corneal surface 15 is modified by removing the volume. The cornea 5 reduced by said volume has an imaging effect modified such that the then corrected focus F* is located on the retina 14. After correction, a modified anterior corneal surface 15* is present, and a correction of defective eyesight is achieved even without spectacles.

Therefore, to define the pattern of the target points, the curvature of the modified anterior corneal surface 15* to be achieved is determined. The starting point for this is the refractive power of the lens 17 of the spectacles, because the determination of the corresponding parameters is a standard method in ophthalmology. The following formula holds true for the refractive power $B_{BR(\varphi)}$ of the lens 17 of the spectacles:

$$B_{BR}(\varphi) = Sph + Cyl \cdot \sin^2(\varphi - \theta). \tag{1}$$

In this equation, Sph and Cyl designate the correction values to be realized for spherical or astigmatic errors of refraction and $\theta$ refers to the position of the cylindrical axis of the cylindrical (astigmatic) eyesight defect, as they are known to the person skilled in the art of optometry. Finally, the parameter $\varphi$ relates to a cylindrical coordinate system of the eye and is counted counter-clockwise, looking towards the eye, as is common in ophthalmology. Now, using the value $B_{BR}$, the curvature of the modified anterior corneal surface 15* is set as follows:

$$R_{CV}^* = 1/((1/R_{CV}) + B_{BR}/(n_c - 1)(1 - d_{HS} \cdot B_{BR}))) + F, \tag{2}$$

In equation (2), $n_c$ refers to the refractive power of the material of the cornea. The corresponding value is usually 1.376; $d_{HS}$ refers to the distance at which spectacles with a refractive power $B_{BR}$ have to be located relative to the corneal vertex, so as to produce the desired correction of defective eyesight by means of spectacles; $B_{BR}$ refers to the aforementioned refractive power of the spectacles according to equation (1). The indication of the refractive power $B_{BR}$ may also cover eyesight defects which go beyond a normal spherical or cylindrical correction. $B_{BR}$ (and, thus, automatically also $R_{CV}^*$) will then show additional coordinate dependencies.

The factor F expresses the optical effect of the change in the thickness of the cornea and can be regarded as a constant factor as a first approximation. For a high-precision correction, the factor can be calculated according to the following equation:

$$F = (1 - 1/n_c) \cdot (d_C^* - d_C), \tag{3}$$

wherein $d_C$ and $d_C^*$, respectively, are the corneal thickness respectively before and after the optical correction. For a precise determination, $R_{CV}^*$ is calculated in an iterative manner by deducting the quantity $(d_C^* - d_C)$ from the difference $(R_{CV}^* - R_{CV})$ during the $i^{th}$ calculation and applying the result of the change in thickness obtained in the $(i+1)^{th}$ calculation. This may be continued until an abortion criterion is fulfilled, for example when the difference of the result for the change in thickness is below a suitably defined limit in two consecutive iteration steps. This limit may be defined, for example, by a constant difference which corresponds to a precision of the refractive correction that is adequate for the treatment.

If the change in thickness of the eye's cornea is neglected, which is, in fact, allowable for a simplified method, F in equation (2) may also be set to zero, i.e., neglected and omitted, for a simplified calculation. Surprisingly, this yields the following simple equation for the refractive power of the modified cornea 5*:

$$B_{CV}^* B_{CV} + B_{BR}(1 - B_{BR} \cdot d_{HS})$$

For the person skilled in the art, the equation $B_{CV}^* = (n-1)/R_{CV}^*$ will easily yield the radius $R_{CV}^*$ of the anterior corneal surface 15* which has to be present after the modification so as to obtain the desired correction of defective eyesight as follows: $R_{CV}^* = 1/((1/R_{CV}) + B_{BR}/((n_c - 1)(1 - d_{HS} \cdot B_{BR})))$.

For the volume, whose removal causes the above change in the curvature of the anterior corneal surface 15, the boundary surface limiting the volume is then determined. In doing so, it is preferably to be taken into consideration that the diameter of the region to be corrected and, thus, the diameter of the volume to be removed should extend, if possible, over the size of the pupil in the dark-adapted eye.

In a first variant, a free form surface is defined by numeric methods known to the person skilled in the art, which surface circumscribes a volume whose removal causes the change in curvature. For this purpose, the change in thickness along the z axis required for the desired modification of the curvature is determined. This will yield the volume as a function of r and $\varphi$ (in cylindrical coordinates), which will in turn yield the boundary surface thereof.

A simple analytic calculation is provided by the following, second variant, wherein the boundary surface of the volume is built up by two partial surfaces, namely an anterior partial surface located towards the corneal surface 15 and a posterior partial surface located opposite. The corresponding relationships are shown in FIGS. 5, 6 and 7. The volume 18 is limited towards the anterior corneal surface 15 by an anterior cut surface 19 which is at a constant distance $d_F$ below the anterior corneal surface 15. With analogy to laser keratomes, this anterior cut surface 19 is also referred to as a flap surface 19, because there, in combination with a cut opening the eye's cornea 5 towards the edge, it serves to enable lifting of a lamella in the form of a "flap" from the underlying cornea 5. This type of removal of the previously isolated volume 18 is also possible here, of course.

The anterior cut surface 19 has a curvature which is located at $d_F$ below the anterior corneal surface 15. If said curvature is spherical, a radius of curvature can be given for the flap surface 19 which is the radius of anterior corneal surface curvature $R_{CV}$ less $d_F$. As will be described later for preferred variants, when generating the cut surface 19, a contact glass can ensure that the anterior corneal surface 15 is spherical at the time the cut surface is generated, so that the pattern of the target points will cause a spherical cut surface. Although the relaxation of the eye 3 after removal of the contact glass may then lead to a non-spherical cut surface 19, the latter will still be at a constant distance from the anterior corneal surface 15 or 15*, respectively. This will be explained later.

The volume 18 to be removed from the cornea 5 is posteriorly limited by a posterior cut surface 20 which, in principle, cannot not be at a constant distance from the anterior corneal surface 15. Therefore, the posterior cut surface 20 will be provided such that the volume 18 is present in the form of a lenticle. For this reason, the posterior cut surface 20 is also referred to as lenticle surface 20. By way of example, said surface is also indicated in FIG. 5 as a spherical surface having a radius of curvature $R_L$, the center of said curvature, of course, not coinciding with the center of curvature of the anterior corneal surface, which is also spherical in FIG. 5.

FIG. 6 shows the conditions after removal of the volume 18. Now, the radius of the modified anterior corneal surface 15* is $R_{CV}^*$ and can be calculated, for example, according to the previously described equations. The thickness $d_L$ of the removed volume 18 is decisive for the change in radius, as made clear by FIG. 7. This figure shows as further quantities the height $h_F$ of the spherical cap defined by the anterior cut surface 19, the height $h_L$ of the spherical cap defined by the posterior cut surface 20 as well as the thickness $d_L$ of the volume 18 to be removed.

Due to the constant distance between the anterior corneal surface and the anterior cut surface 19, the posterior cut surface determines the curvature of the anterior corneal surface 15* after removal of the volume 18. Thus, for example, in the case of a correction of defective eyesight taking cylindrical parameters into consideration, the posterior cut surface 20 will have an angularly dependent radius of curvature. The following generally applies for the lenticle surface 20 shown in FIG. 7:

$$R_L(\varphi) = R_{CV}^*(\varphi) - d_F,$$

or in cylindrical coordinates ($z$, $r$, $\varphi$):

$$z_L(r,\varphi) = R_L(\varphi) - (R_L^2(\varphi) - r^2)^{1/2} + d_L + d_F.$$

If astigmatism is not to be taken into consideration, the dependence on $\varphi$ will not occur and the lenticle surface 20 becomes spherical. However, assuming a need for a cylindrical correction of defective eyesight, the lenticle surface 20 usually has different radiuses of curvature on different axes, although these will generally have the same vertex, of course.

This further implies automatically that the theoretical intersection line between the flap surface 19 and the lenticle surface 20 will not be located in a plane, i.e. at constant z coordinates, in the case of a cylindrical correction. The smallest radius of curvature of the lenticle surface 20 is at $\varphi = \theta + \pi/2$ and the greatest on the axis $\theta$ of the cylindrical eyesight defect, of course, i.e. at $\varphi = \theta$. In the case of a correction of hyperopia, unlike the representation in FIG. 7, the vertex of the flap surface 19 and the lenticle surface 20 coincide and the lenticle surface 20 has a stronger curvature than the flap surface 19. The thickness $d_L$ of the lenticle results as the rim thickness.

The volume 18, which is to be construed as a lenticle, has the smallest rim thickness at $\varphi = \theta = \pi/2$, because the lenticle surface 20 and the flap surface 19 intersect there. For all other values of $\varphi$ a finite rim thickness is given if a given z coordinate is assumed as the lower limit of the lenticle surface 20.

Alternatively, an additional rim surface can be provided in addition to the flap surface 20 and the lenticle surface 19, said additional rim surface circumscribing the volume 18 in the region of intersection of the flap surface 20 and the lenticle surface 19 or connecting these surfaces, respectively, at points which do not converge at given z coordinates. Cutting of this rim surface is also affected by the pulsed laser beam. For example, the rim surface may have a cylindrical shape, an elliptical shape (in a top view) or a conical shape (in a lateral view).

The design of the volume 18 as being limited by an anterior cut surface 19 at a constant distance from the anterior corneal surface 15 as well as by a posterior cut surface 20 is only one variant for limiting the volume 18. However, it has the advantage that the optical correction is substantially defined only by one surface (the lenticle surface 20) so that the analytical description of the other partial surface of the boundary surface is simple.

Further, optimum safety margins are provided with respect to the distance of the volume to the anterior corneal surface 15 and the posterior corneal surface 16. The residual thickness $d_F$ between the anterior cut surface 19 and the anterior corneal surface 15 may be set to a constant value of, for example, 50 to 200 µm. In particular, said thickness may be selected such that the epithelium, which is sensitive to pain, remains within the lamella formed by the flap surface 19 below the anterior corneal surface 15. Also, the design of the spherical flap surface 19 is in continuity with previous keratometer cuts, which is advantageous for the acceptance of the method.

After generating the cut surface 19 and 20, the volume 18 thus isolated is then removed from the cornea 5. This is schematically represented in FIG. 8, which further shows that the cut surfaces 19 and 20 are generated by the influence of the treatment laser beam incident in a focus cone 21, for example by sequential arrangement of plasma bubbles, so that the flap cut surface 19 and the lenticle cut surface 20, in a preferred embodiment, are generated by suitable three-dimensional shifting of the focus position of the pulsed laser radiation 2.

As an alternative, only the flap surface 19 may be formed, in a simplified embodiment, by target points defining the curved cut surface 19 at a constant distance from the anterior corneal surface 15, by means of pulsed laser radiation, and removal of the volume 18 is effected by laser ablation, for example by the use of an excimer laser beam. For this purpose, the lenticle surface 20 can be defined as the boundary surface of such removal, although this is not mandatory. In this respect, the treatment apparatus 1 works like a known laser keratome; however, the cut surface 19 is produced on curved cornea. The features described above and below, respectively, are also possible in such variants, especially with respect to the determination of the boundary surface, its geometric definition and the determination of control parameters.

If both the lenticle surface 20 and the flap surface 19 are generated by means of pulsed laser radiation, it is convenient to generate first the lenticle surface 20 and second the flap surface 19, because the optical result in the lenticle surface 20 will be better (or even achieved in the first place), if no change of the cornea 5 has occurred above the lenticle surface 20 yet.

Figure 8:
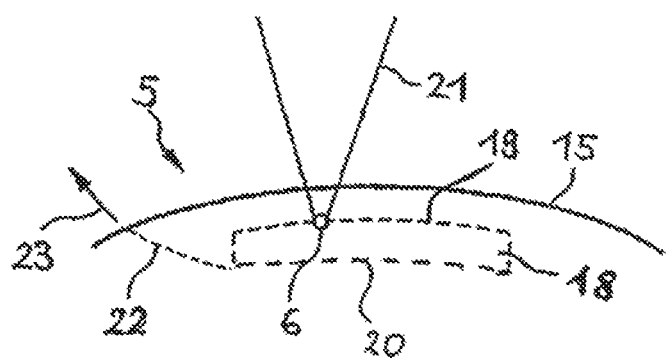
FIG. 8 shows a schematic sectional view through the eye's cornea illustrating the removal of said volume.

The removal of the volume 18 by the pulsed laser radiation can be achieved, as indicated in FIG. 8, by a peripheral cut 22, allowing to extract the volume 18 in the direction of an arrow 23 shown in FIG. 8. However, as an alternative, the peripheral cut 22 may be provided such that it connects the anterior cut surface 19, i.e., the flap surface 19, with the anterior corneal surface 15, thereby forming a ring, although said peripheral cut does not extend fully around an angle of 360°. The lamella isolated in this way remains connected to the residual tissue of the cornea 5 in a narrow region. This connecting bridge will then serve as a hinge, so as to be able to fold the otherwise isolated lamella away from the cornea 5 and to remove from the rest of the eye's cornea 5 the already isolated volume 18 made accessible in this manner. The position of the connecting bridge can be predetermined when generating the control data or the target points, respectively. Thus, the described method or apparatus, respectively, realizes, according to this aspect, the isolation of the volume 19 within the cornea 5 and generates a flap, connected with the rest of the eye's cornea via a tissue bridge, as a lid over the volume. Said lid can be folded away and the volume 18 can be removed.

To generated the cut surfaces 19 and 20, the target points can easily be arranged in various ways. The prior art, for example WO 2005/011546, discloses special spirals to generate cut surfaces in the eye's cornea, which spirals extend, for example, in the manner of a helical line around a main axis being substantially perpendicular to the optical axis (z axis). Also, the use of a scanning pattern is known which arranges the target points in lines (cf. WO 2005/011545). Of course, these options can be used to generate the above-defined cut surfaces and can be employed with by the below-explained transformations.

The adjustment of the position of the focus in the eye's cornea is effected by means of the three-dimensional deflecting device schematically shown in FIG. 3, which device employs the shifting of lenses or other optically effective elements to adjust the focus in the z direction. However, the adjustment of lenses or the like is usually not feasible as fast as the swiveling of mirrors which are usually used in the xy scanner. Therefore, the speed of adjustment of the z scanner generally limits the rate at which the cut surfaces can be generated in the eye's cornea. In order to generate the cut surfaces 18 and 19 as quickly as possible, the focus is, therefore, in a preferred embodiment, guided along a spiral-shaped path, with one spiral each being located in the spatially curved cut surface. Thus, while writing the spiral, the z scanner is adjusted such that the arms of the spiral follow the spatially curved cut surface.

Figure 9:
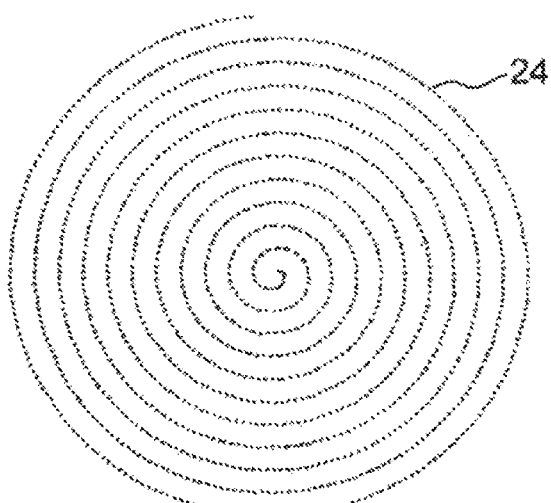
FIG. 9 shows a top view of a spiral-shaped path curve used to isolate the volume of FIGS. 5, 7 and 8.
Figure 10:
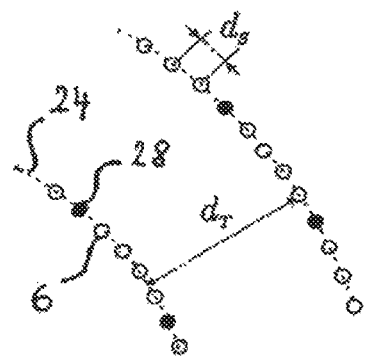
FIG. 10 shows an enlarged view of the path curve of FIG. 9.

By way of example FIG. 9 shows a path curve 24 as a spiral, which is a circular spiral in the representation shown. The radius of the planar spiral shown increases in circular coordinates as the angle of rotation φ increases, so that:

$$r(\varphi) = \varphi \cdot d_T / (2\pi) \quad (4)$$

holds. In this equation, $d_T$ is the distance of the spiral arms; it is shown in FIG. 10, which depicts an enlarged detail of FIG. 9. The distance of the individual spots 6 onto which the pulsed laser radiation is focused and at which a plasma bubble, for example, is generated by a laser pulse constantly equals $d_S$ in the spiral, so that the angular spacing Δφ of the individual spots 6 at which a laser pulse is introduced into the tissue is:

$$\Delta\varphi = d_S / r$$

Figure 11:
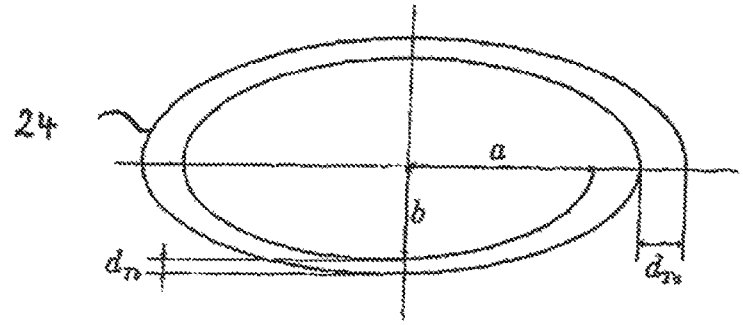
FIG. 11 shows an alternative path curve for the correction even of cylindrical eyesight defects.

Since the lenticle surface 20, as already mentioned, is usually not non-spherical, the path curve 24 along which the laser focus is adjusted is an elliptical spiral for which obviously no constant distance of the spiral arms exists. However, along the main axes a and b, a respective path distance $d_{Tb}$ as well as $d_{Ta}$ may be defined, as shown in FIG. 11.

FIG. 10 shows the spots 6 so as to make clear the position of the focus of the individual laser pulses. Of course, the plasma bubbles actually expand after introduction of the respective laser pulse to such extent that the cut surface is generated, and the path curve 24 is then no longer visible in the cut surface.

For preparation of the surgical method, the definition of the path curves 24 by which the cut surfaces are generated has to be effected after definition of the cut surfaces 19 and 20.

Figure 12:
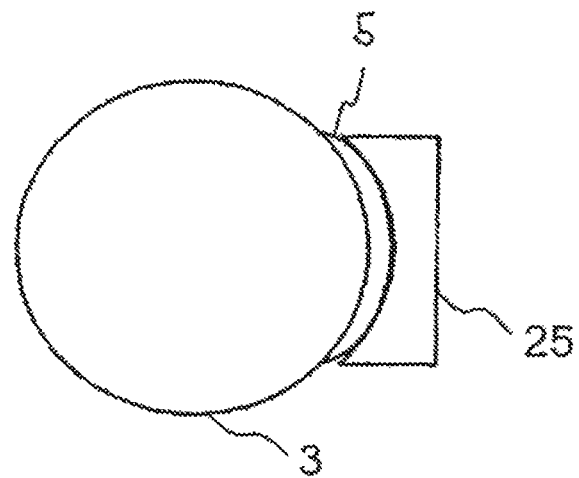
FIG. 12 shows a schematic representation explaining the function of the contact glass in the treatment apparatus of FIG. 1, FIGS. 13 to 15 show schematic representations with respect to the effects of the contact glass by deformation of the eye's cornea.

Of course, when determining the path curves 24, it should be noted that finally the volume 18 is to be defined for the eye under normal conditions. The cut surfaces 19 and 20 as explained so far relate to the natural eye. However, it should be taken into account that the treatment apparatus 1 uses a contact glass 25 for fixation of the eye, which contact glass 25 is placed on the anterior corneal surface 15 of the eye's cornea 5, as shown in FIG. 12. The contact glass 25, which is already the subject of several patent publications (by way of example, reference is made e.g., to WO 2005/048895 A), is of interest for the present description of the treatment apparatus 1 or the related methods, respectively, for preparing and/or carrying out the surgical operation only insofar as it imparts to the anterior corneal surface 15 a defined curvature, on the one hand, and as it spatially keeps the eye's cornea 5 in a predefined position relative to the treatment apparatus 1, on the other hand. With respect to the spherical curvature of the contact glass 25, however, the approach described herein differs considerably from the approach as described, for example, in WO 2003/002008 A, which uses a planar contact glass pressing the eye's cornea flat.

Figure 13:
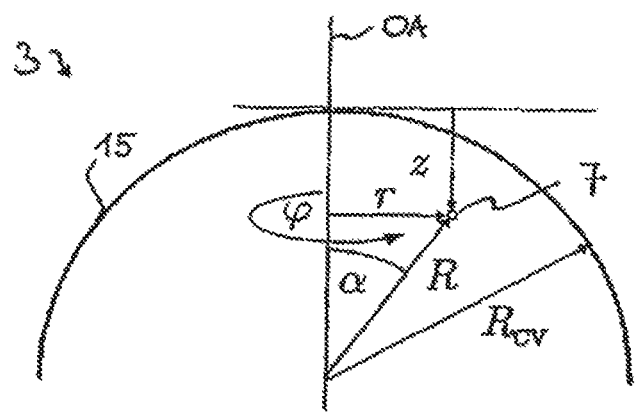
Figure 14:
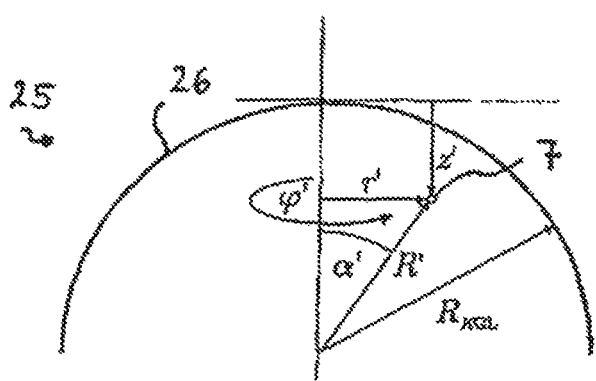

When the eye is pressed against the contact glass 25 having a spherical contact surface, spatial deformation of the eye occurs. Since the cornea is usually compressible only tangentially, i.e. does not change its thickness when pressing is done in this manner, said pressing corresponds to a transformation of the eye's coordinate system, as shown in FIG. 13, into the coordinate system of the contact glass shown in FIG. 14. This context is known to the person skilled in the art from WO 2005/011547 A1, whose disclosure is incorporated herein by full reference in this respect. In FIGS. 13 and 14, any coordinates provided with an apostrophe designate the coordinates of quantities relating to the contact glass 25 or to the contact glass bottom surface 26 facing the eye.

Moreover, the contact glass has a still further advantage. Due to the pressing onto the spherical contact glass bottom surface 26, the anterior corneal surface 15 becomes automatically spherical. Thus, the anterior cut surface 19 located at a constant distance below the cornea's anterior surface 15 is also spherical due to the pressing of the contact glass, which sphericity leads to a considerably simplified control. Therefore, completely independently of other features, it is preferred for the invention to use a contact glass 25 having a spherical contact glass bottom surface 26 and to limit the volume by an anterior cut surface 19 as well as by a posterior cut surface, predetermining target points for the anterior cut surface which form said cut surface as a spherical surface at a constant distance $d_F$ below the anterior corneal surface 15. For the posterior cut surface, target points are/are being predetermined which define for the relaxed eye, i.e., after removal of the contact glass, a curvature corresponding to that which is desired for the correction of defective eyesight, except for the distance $d_F$ from the anterior corneal surface. Analogous considerations apply to the method for defining the target points or to the method of surgical operation.

The representations in FIGS. 13 and 14 shows the coordinate transformation which occurs at the eye when fitting or removing the contact glass, respectively. They contain both spherical coordinates (R, α, φ) referring to the origin of the curved surface (anterior corneal surface 15 or contact glass bottom surface 26) and cylindrical coordinates (r, z, φ) referring to the vertex of the anterior corneal surface 15 or of the contact glass bottom surface 26, respectively, said vertex being defined by the point where the optical axis OA intersects.

Figure 15:
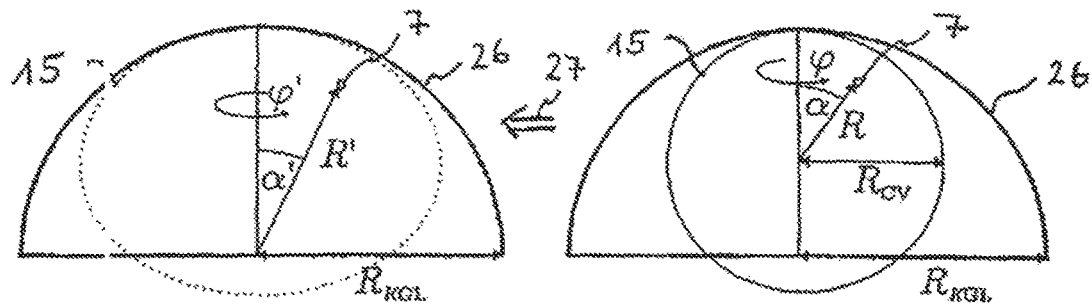

During the coordinate transformation from the coordinate system referring to the eye, as shown in FIG. 13, to the system referring to the contact glass, according to FIG. 14, the arc length, i.e. α·R, the radial depth ($R_{CV}$–R) as well as the angle φ remain unchanged. Thus, the transformation of the shapes of the cut surfaces 19 and 20 used as the basis for the natural eye, i.e. in the coordinate system of FIG. 13, is an important step in the calculation of the control factors for the three-dimensional focus adjustment device. The calculation is basically different than for a planar contact glass, wherein e.g., the flap surface 19 degenerates to a plane. Substantially only the shape of the cut surface 20 has to be transformed because the cut surface 19 merely has to be generated at a constant distance $d_F$ from the anterior corneal surface 15. Thus, in the transformed system, the cut surface 19 is a sphere having a radius of curvature $R_F$ which is reduced with respect to the curvature radius of the contact glass bottom surface. The pressing of the cornea 5 of the eye 3 against the spherically curved contact glass bottom surface 26 is illustrated in FIG. 15. There, the representation on the right-hand side schematically shows the condition when the contact glass bottom surface 26 touches the anterior corneal surface at the vertex. For a clearer illustration of the geometric relationships, the anterior corneal surface 15 is schematically drawn as a circle in FIG. 15, although the curvature is spherical only within a smaller circle segment, of course. Pressing the contact glass 25 onto the cornea 5 causes the transition, symbolized by the arrow 27, to the condition on the left-hand side of FIG. 15. Removal of the contact glass 25 causes a relaxation of the eye 3 in the opposite direction of the arrow 27.

Due to the conditions mentioned above, the coordinates for each point in the eye's cornea 5 transform from the system shown in FIG. 13 to the system of FIG. 14. Now, this is used as a basis for selecting the control factors for the focus adjustment such that the cut surfaces 19 and 20 are to be described in the transformed contact glass system, because only then will they have the desired shapes after removal of the contact glass 26, i.e., after being transformed back to the natural coordinate system of the eye. Since contacting of the anterior corneal surface 15 is usually effected by suction, the aforementioned transformation will be referred to hereinafter also as suction transformation.

Now, in order to cut the flap surface 19, which is spherical as mentioned above, the following speed of adjustment of the z scanner, i.e., the following feed rate in the z direction, is set:

$$v_Z(t) = d_S \cdot f_L \cdot d_T / (2\pi \cdot (R_F^2 - t \cdot d_S \cdot f_L \cdot d_T / \pi))^{1/2}, \quad (5)$$

wherein $f_L$ is the frequency of the laser pulses of the laser radiation 2. Equation (5) requires that the z speed $v_Z$ can be freely set and continuously changed.

If it is desired to write a sphere at a speed $v_Z$, which is selected from a group of discrete speeds, which is usually the case if the z scanner is driven by a stepping motor, the time dependence of the radial function r(t) will be obtained as:

$$r(t) = [d_S \cdot f_L \cdot d_T \cdot t / \pi - (d_S \cdot f_L d_T \cdot t)^2 / (2\pi \cdot R_F)^2]^{1/2} \quad (6)$$

as well as, for the angular function, $$\varphi(t) = [4\pi \cdot d_S \cdot f_L \cdot t / d_T - (d_S \cdot f_L \cdot t)^2 / R^2]^{1/2}. \quad (7)$$

The $t^2$ terms under the square root of the radial function as well as of the angular function show that no ideal Archimedian spiral is written anymore, i.e., the path and spot bubble distances vary in favor of the z speed being variable only in steps.

If a constant z feed is desired for the focus adjustment, this will not result in a sphere, as with the speed according to equation (4), but in a paraboloid, and the following holds true:

$$z(r) = [v_Z / (d_S \cdot d_r)][r^2 \cdot \pi / f_L] \quad (8)$$

As mentioned, in some treatment apparatuses 1, the speed at which the z scanner shifts the focus in the z direction can be adjusted only within a set of discrete speeds. If it is then desired to write a specific parabola by a given speed $v_Z$, the product $d_S \cdot d_T$ has to be selected accordingly, so that the expression in the first square brackets of the equation (8) has the desired value. The distance of the paths, defined by $d_T$, as well as the spot distance along the path described by $d_S$, are consequently suitable to vary so as to write a specific parabola at given $v_Z$.

Any of the equations (5), (6)/(7) and (8) can be used to determine the target points and, thus, the control of the focus adjustment, in which case the corresponding spiral shape/surface shape then has to be used as a basis, of course. Where it is mentioned below that the equations are used for control, this means, in particular, that the target points are determined by means of the equations, which can be effected, for example, by evaluating the functional equations at equidistant points in time. In one variant of the invention, the speed equations are used to ensure that the determined target points do not require adjustment speeds which cannot even be realized by the focus adjustment device.

For the shapes of the surfaces 19 and 20 mentioned above and determined as described, a spiral is fitted to the respective surface. The spiral is written under control as described. The calculation of the z speed as well as of the r- and φ-speeds takes into consideration the surface shape of the surface 19 or 20, respectively.

The lenticle surface 20 is spherical if no cylindrical correction is to be performed. Therefore, one uses control according to equations (4)/(5) or (6)/(7) to generate such sphere. However, as is known, a sphere can also be approximated by a paraboloid. Therefore, it is envisaged, according to one inventive variant, to approximate one sphere by a paraboloid in a manner known to the person skilled in the art and to perform control according to equation (8).

Due to the suction transformation according to FIG. 15, the geometry of the lenticle surface 20 changes. The lenticle surface 20 has to have the curvature of the corrected anterior corneal surface 15* in the coordinate system of the contact glass 25. It cannot be related to a center of curvature which coincides with the center of curvature of the contact glass. The curvature defined according to the equation (2) is, thus, converted with respect to the suction transformation.

Of course, the radius of curvature defined in equation (2) is a function of φ. As already mentioned and as common in ophthalmology, two radiuses of curvature $r_a$ and $r_b$ can be given, respectively: one on the axis θ of the cylindrical eyesight defect and one for an axis perpendicular thereto. Computationally, it is particularly favorable to approximate a toroidal curvature, which thus results in the general case, by a parabola such that the lenticle surface 20 is approximated by a paraboloid. This is preferably affected prior to the contact pressure transformation, but may also be carried out thereafter.

Figure 16:
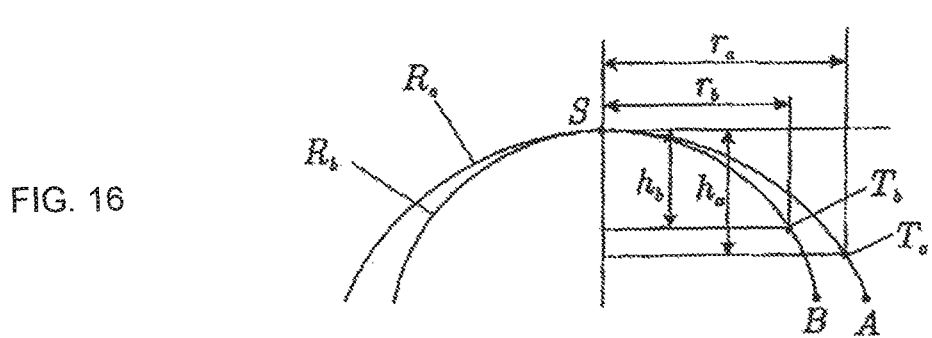
FIGS. 16 and 17 show schematic views relating to the approximation of the volume of the surface posteriorly limiting the volume in the case of corrections even of cylindrical eyesight defects.

Said approximation is effected by searching a respective parabola for the two radiuses of curvature which extends both through the vertex of the lenticle surface 20 and through a point located, if possible, at the rim. FIG. 16 shows the corresponding conditions in the coordinate system of the eye. This figure shows the spherical lenticle surface 20 prior to the contact pressure transformation. In the figure, the sections through the lenticle surface 20, which is toroidal in the generalized case, are superimposed on one another along the two half-axes a and b. The corresponding curves are referred to as A and B and are circular, with a radius of curvature $r_a$ and $r_b$, respectively. On each curve, a rim point T is described in cylindrical coordinates by the corresponding radius r as well as the height, these parameters referring to the vertex S which is identical for both half-axis sections. Thus, the point $T_a$ is characterized by the radius $r_a$ as well as the height $h_a$. This applies analogously to $T_b$.

Now, a parabola is being searched for, which satisfies $h=k \cdot r^2$. The parabola parameters $h_a$ obtained thereby for the parabola along the semimajor axis a as well as $k_b$ for the parabola along the semiminor axis b define the paraboloid, which is then written while shifting the focal point in the z direction, e.g. by means of a constant z feed (cf. equation (7)) or which is selected from a set of discrete speeds when selecting the z speed (modification of equation (7)). The sections shown in FIG. 16 of the toroidal lenticle surface 20 along the semiminor axis b as well as the semimajor axis a refer to the representation in the coordinate system of the eye.

Figure 17:
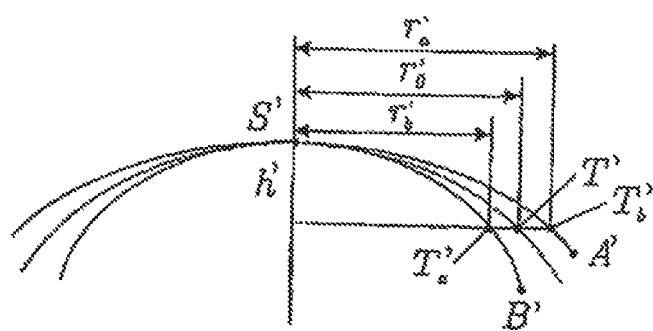

If the approximation has been carried out by parabola equations after the contact pressure transformation, the transformed values will appear there, of course. The explicit calculation of transformed values can be avoided at this point, if the approximation is effected first and the parabola parameters thus found for the contact pressure transformation are subjected to the coordinate system of the contact glass, whereafter the conditions shown in FIG. 17 are then present.

The specification of the parabola parameters in the coordinate system of the eye according to FIG. 16 is as follows:

$$k_a = (z(T_a) - z(S))/r(T_a)^2, \quad (9)$$

$$k_b = (z(T_b) - z(S))/r(T_b)^2. \quad (10)$$

In equations (9) and (10), z(S) refers to the z coordinate of the point S. Placing the origin of the coordinate system in the vertex, as in the previous figures, the z coordinate will be zero. The coordinate $z(T_a)$ or $z(T_b)$, respectively, as well as $r(T_a)$ or $r(T_b)$, respectively, are the z or r-coordinates, respectively, of the corresponding point $T_a$ or $T_b$, respectively, in the cylindrical coordinate system.

If the parabola parameters $k_a$ or $k_b$, respectively, are not needed in the coordinate system of the eye according to FIG. 16, but in the coordinate system of the contact glass according to FIG. 17, the points S, $T_a$ and $T_a$ will then be replaced by the transformed points S', $T_a'$, $T_b'$ indicated in FIG. 17.

Now, in order to represent the lenticle surface 20 in the pressure-contacted eye 3 by a (then usually elliptical) spiral with semi axes $r_a'$ and $r_b'$, said spiral is constructed from a circular spiral of radius $r_0'$ by elongation in the direction $\varphi=\theta$ and compression in the direction $\varphi=\theta+\pi/2$. Due to the simultaneous elongation and compression, the average path or spot distance, respectively, is maintained. If compression or elongation were affected only in one direction, the average distance would change.

The actual radiuses can be calculated as follows from the radius $r_0$ of the circular spiral, which is shown in broken lines in FIG. 17, with the help of ellipticity:

$$e' = r_a'/r_b' = (k_B'/k_a')^{1/2}.$$

The ellipticity e' is the ellipticity of the transformed toroidal lenticle surface 20. The parameters $k_b'$ as well as $k_a'$ are given by the equations (11) and (12) for the transformed points S', $T_a'$ and $T_b'$, respectively. The parabola parameters result from the fact that the circular spiral of radius $r_0$, from which the lenticle surface 20 is constructed here, is intended to be an arithmetic or geometric average of the curvatures of the great and small half-axes of the paraboloid, respectively.

$r_0' = (r_a' \cdot r_b')^{1/2}$ yields $k = (k_a \cdot k_b)^{1/2}$ for the parabola parameter, as well as the main axes of the ellipse: $r_a' = r_0' \cdot (e')^{1/2}$ and $r_b' = r_0' \cdot (e')^{-1/2}$.

At this point of the determination of the target points, two path curves 24 are obtained, which are described by functional equations. The pattern of the target points is determined by evaluation of these functional equations.

However, it remains to be considered that the focusing of the laser beam in the focus 7 is subject to a focus position error. This focus position error is a property of the optical system, i.e. results from the optical realization used. It is governed substantially by the optical design. Moreover, due to limited manufacturing accuracy within the allowed tolerances, the focus position error is apparatus-specific. Therefore, it is convenient to determine said error individually for each apparatus.

Accounting for the focus position error is effected by a usually non-linear transformation (referred to hereinafter also as NL transformation), which makes it impossible to carry out the NL transformation by modification of the path curve parameters. In a preferred embodiment of the invention, the focus position error is expressed by a correction table or a correction function. Said function is derived from gauging the optics of the treatment apparatus 1. Such gauging can be effected for a type of apparatus or individually for each apparatus. The correction function can be obtained by interpolation of the results of gauging, e.g., by means of polynomials or splines. The focus position error is generally rotationally symmetric with respect to the optical axis. It will then depend only on r and z in cylindrical coordinates.

The points previously calculated by means of the path curves are pre-distorted in the NL transformation such that they are located exactly at the desired location after introduction of the laser spot by the optical system having said focus position error. Thus, the application of the pre-distorted coordinates compensates for the focus position error appearing in the optical system.

Figure 18:
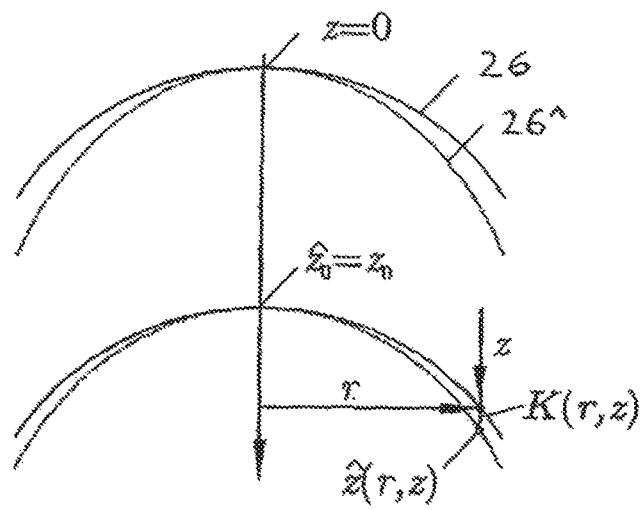
FIG. 18 shows a schematic view of a correction of the image field curvature as applied when determining control data for the treatment apparatus of FIG. 1.

The NL transformation is based on the idea that for each point having the coordinates (z, r) a contact glass sphere, displaced by $z_0$, can be found, on which this point is located. The vertex of said sphere is then exactly at $z_0(z, r) = z - z_{KGL}(r)$. The effect of the pre-distortion in compensating the focus position error is illustrated in FIG. 18. It shows the contact glass bottom surface 26, which is spherical in the present example, but may also have any other shape. Due to said pre-distortion, said sphere becomes a transformed contact glass sphere 26^. The parameters taking the pre-distortion of the focus position error into consideration are symbolized in FIG. 18 by adding a roof-like symbol "^" to them. In this case, $z_0^{\wedge} = z_0$ holds true for a transformed axial point in the cornea. This allows for the fact that, although the focus position error is rotationally symmetric in most cases, it also results in a shift along the z direction.

For pre-distortion, the calculated path curves are converted to individual target point coordinates for the spots, which are then shifted in the correction transformation, i.e., the NL transformation, symbolized by K(r, z) in FIG. 18. If the focus position error is indicated as function K, the coordinate of each target point merely has to be evaluated by said function to obtain the shift or the transformed coordinate, respectively.

As a result, a respective set of target points is present for the surfaces 19 and 20, along which points the focus is guided. Due to the NL transformation and the contact pressure transformation, the coordinates with respect to the natural, i.e., free, eye are located precisely in the desired anterior and posterior cut surfaces 19, 20.

The coordinates thus obtained for the target points further have to be converted to control signals for the three-dimensional deflecting unit, e.g., the xy-scanners as well as the z scanner. For this purpose, a corresponding functional relationship or a corresponding characteristic map is used, which is known for the scanners and has been previously determined, where applicable.

In particular, the response function was previously determined, in particular, for the xy-scanners, which are realized as galvanometer mirrors in the exemplary embodiment. By applying a frequency sweep to the galvanometer mirrors as well as measuring the actual galvanometer movement, an amplitude response function and a phase response function will be obtained. These will be factored in determining the control signals.

To simplify control, not every target point results in a respective aiming point for the scanners. Instead, the control device 12 uses sample points to characterize the path of the scanner. The number of points is reduced considerably thereby. This may be benefited from already during the NL transformation, by subjecting to said transformation only those target points of the path curves which are intended to be sample points for control. Thus, according to one embodiment of the invention, evaluation of the functional equations is effected by means of a time interval which is larger than the time interval between the laser pulses.

Thus, prior to the NL transformation, the path curve points are filtered to provide the aforementioned nodes, i.e., points occurring at a frequency of the scanner control, for the transformation. An equivalent to such filtering is an evaluation of the functionally described path curves at nodes, which are spaced apart in accordance with the scanner control. This reveals a further advantage of the function-based approach described herein: The decision, which points are target points for controlling the focus adjustment device, has to be made no sooner than prior to the NL transformation. Before, only the path parameters have to be converted in a suitable manner. Also, datasets comprising a multiplicity of points will not occur until then.

Thus, the sample points define target points which are only a subset of the set of points to which a laser pulse is emitted. This is illustrated in FIG. 10, in which those spots 6, which exist in the control dataset as target points 28, are shown as solid black circles.

This approach further has the advantage that the maximum frequency $f_S$, which occurs during control of the scanner, is considerably smaller than the laser pulse frequency $f_p$. For example, a control frequency of 20 kHz as well as a laser pulse frequency of 200 kHz can be worked with. This has the result that one or more spots 6 onto which pulsed laser radiation is also emitted are located between the target points 28 provided to control the scanner.

Thus, there is not only an emission of pulsed laser radiation while the scanners are being subjected to an adjustment operation, e.g., while the galvanometer mirrors are moving, but laser pulses are deflected by the scanners while the latter are moving from one predetermined target point to the next. In order to achieve a maximum speed of deflection, this movement represents an oscillation which, in the case of perfect circular spirals (as they occur in the anterior cut surface 19), is even a purely sinusoidal oscillation. Since, in the case of the lenticle surface 20, too, the actual spiral shape deviates only slightly from ideal circular or elliptical spirals, the scanners can be operated at near their maximum frequency, so that the written paths along which the spots are arranged allow very quick production of cut surfaces.

Determining the control datasets which contain the target points from the above-described sets of points, which were obtained for the path curves, completes the preliminary procedure, which was carried out so as to generate the corresponding control values or control parameters. This preliminary procedure requires no human intervention and, in particular, no intervention from a physician or surgeon. The method is carried out by the control device 12 without any action by a physician. The physician's presence is not required until the subsequent surgical operation.

Figure 19:
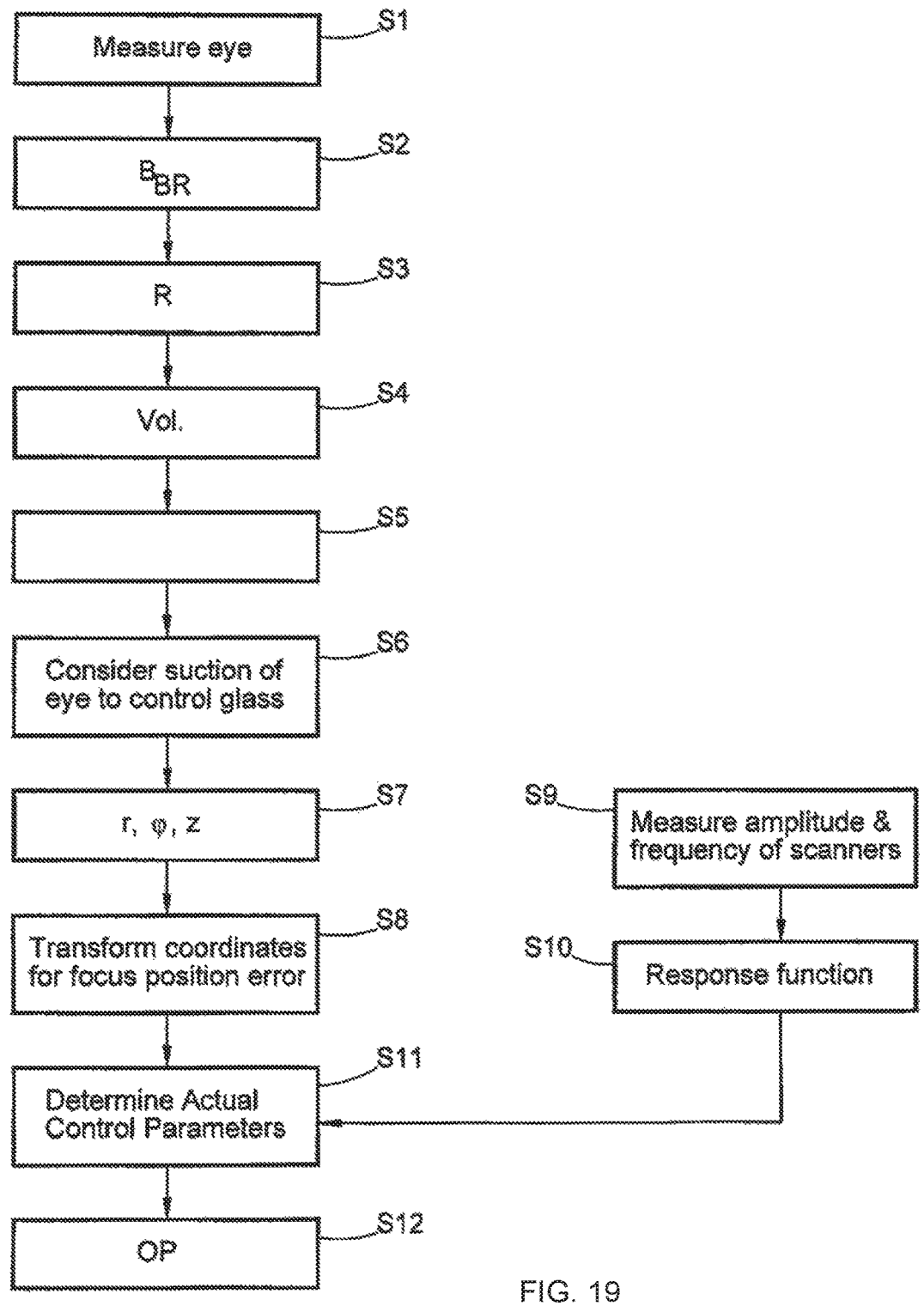
FIG. 19 shows a schematic representation of the sequence of preparing and carrying out a correction of defective eyesight.

The procedure of the method for preparing the apparatus 1 for use in an ophthalmic operation of defective eyesight is schematically summarized in FIG. 19. In a step S1, the eye 3 is measured. In doing so, correction parameters such as those which are common for conventional spectacles, for example, are obtained for the eyesight defect of the patient 4. The parameters established in step S2 are then used, in a step S3, to determine the new curvature of the cornea 5 required for the corrected eye. Once this calculation in step S3 has been completed, the volume which is to be removed from the cornea is determined in S4. This is usually done by defining the lenticle surface 20 as well as the flap surface 19 in a step S5. Once the corresponding functional descriptions of these surfaces have been achieved, the suction transformation, which is effective in sucking the eye to the contact glass, is taken into consideration in step S6.

Next, the coordinates of the path curves, from which the cut surfaces are constructed, are determined. This is schematically indicated in step S7 by the parameters r, φ, z. At the end of step S7, a point pattern is present, comprising the coordinates of the spots on which a laser radiation pulse is to act. The density of the target points can already be reduced to simplify the calculation effort. For this purpose, when controlling the scanners, not every spot to which laser radiation is applied is a sample point.

In the following, the set of coordinates thus obtained is transformed again in step S8 to allow for the focus position error. Then, in a step S11, the actual control parameters are determined, including a response function, which was obtained in a step S10 from a previous measurement (step S9) of the amplitude behavior and frequency behavior of the scanners.

Using the thus-determined control parameters, the actual operation is then performed in step S12, during which operation additional spots, preferably located between the individual locations of support upon which the control of the scanners is based, are irradiated with laser radiation pulses.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A treatment apparatus for ophthalmic surgery of an eye of a patient, said apparatus comprising:
   a laser device including a laser source emitting pulsed treatment laser radiation;
   a focusing device that focuses the treatment laser radiation to a focus position located in the eye;
   a scanner that shifts the focus position and
   a control device operably coupled to the scanner and configured to control the scanner by specifying a pattern of target points located within the eye such that a cut is generated within the eye,
   wherein the control device is further configured to introduce a point of aim in form of a pre-offset for at least some of the specified target points which point of aim differs from a desired final focus position by a spatial difference selected to compensate for focus position errors generated by the focusing device, and
   wherein the spatial difference depends on a position of a respective target point.

2. The apparatus of claim 1, wherein the control device is further configured to determine said spatial difference by accessing a correction table or function which indicates the focus position error as a function of the position of the respective target point.

3. The apparatus of claim 1, wherein the spatial difference shifts the point of aim against the desired final focus position in parallel with an optical axis.

4. The apparatus of claim 2, wherein the correction table or function depends only on axial and radial coordinates (r, z).

5. The apparatus of claim 1, wherein the control device is further configured to define a path along which the focus position is to be shifted, to define the pattern by selecting points located on the path as focus position target points and to determine the spatial differences for the selected points.

6. The apparatus of claim 5, wherein the control device is further configured to define the path by at least one functional equation and to determine the target points by evaluation of said at least one functional equation.

7. The apparatus of claim 1, wherein the control device is further configured to take a deformation of the eye into consideration, which deformation occurs during irradiation of the treatment laser radiation, due to a contact glass pressed onto the eye.

8. The apparatus of claim 5, wherein the control device is further configured to first define the path relating to the eye in an undeformed state and to modify said path so as to compensate for the deformation of the eye.

9. The apparatus of claim 7, wherein the control device is further configured to first define the path relating to the eye in an undeformed state and to modify said path so as to compensate for the deformation of the eye.

10. The apparatus of claim 1, further comprising a contact glass deforming a front face of the eye, wherein the control device is further configured to receive focus position data for a shape of a cut to be generated in the eye, which shape is defined for the front face of the eye in a natural and undeformed state, and to transform the focus position data to compensate for the deformation of the front face of the eye imparted by the contact glass.

11. The apparatus of claim 10, wherein the contact glass is spherical and the control device is further configured to keep an arc length, a radial depth and an angle unchanged when transforming the focus position data.

12. The apparatus of claim 1, wherein
    the focusing device is further configured to focus the treatment laser radiation to a cornea of the eye, and
    the control device is further configured to create the cut to isolate a volume in the cornea, the removal of said volume from the cornea causing a change in radius of curvature of an anterior corneal surface to correct defective eyesight, wherein the changed radius of curvature $R_{CV}^*$ satisfies the equation $$R_{CV}^* = 1/((1/R_{CV}) + B_{BR}/((n_c-1)(1-d_{HS} \cdot B_{BR}))) + F,$$

wherein $R_{CV}$ is the radius of curvature of the anterior corneal surface before removal of the volume, $n_c$ is a refractive power of material of the cornea, F is a correction factor, $B_{BR}$ is a refractive power of spectacles suitable for correction of the defective eyesight, and $d_{HS}$ is a distance at which the spectacles having the refractive power $B_{BR}$ should be located anterior of a corneal vertex in order to achieve the desired correction of defective eyesight by means of the spectacles.

13. The apparatus of claim 12, wherein the control device is further configured such that
    $F=(1-1/n_c) \cdot (d_c^*-d_c)$ holds true, wherein $d_c$ is the thickness of the cornea before removal of a volume, $d_c^*$ is the thickness of the cornea after removal of the volume, and
    the control device is further configured to calculate the radius $R_{CV}^*$ iteratively by deriving a change in thickness $(d_c^*-d_c)$ from difference $(R_{CV}^*-R_{CV})$ in each iteration step, and by applying a result thus obtained for a change in thickness, when calculating $R_{CV}^*$ in a next iteration step.

14. The apparatus of claim 12, wherein the control device is further configured such that, in order compensate for a cylindrical eyesight defect of the eye (3), the radius $R_{CV}^*$ is a function of a cylindrical angle $\Phi$, i.e. $R_{CV}^*(\Phi)=1/((1/R_{CV}(\Phi))+B_{BR}(\Phi)/((n_c-1)(1-d_{HS} \cdot B_{BR}(\Phi))))+F$ holds true.

15. The apparatus of claim 12, wherein the control device is further configured such that the cut confines the volume by a boundary surface, which comprises an anterior cut part and a posterior cut part, wherein the anterior cut part is located at a constant spacing $d_F$ from the anterior corneal surface, but the posterior cut part is not.

16. The apparatus of claim 15, wherein the control device is further configured such that the posterior cut part is curved and has a radius of curvature satisfying $R_L = R_{CV}^* - d_F$.

17. The apparatus of claim 15, wherein the control device is further configured such that the posterior cut part, in cylindrical coordinates $(z, r, \varphi)$ having an origin located at a point where an axis of vision of the eye passes through an anterior corneal surface, satisfies an equation $Z_L(r,\Phi) = R_L(\varphi) - (R_L^2(\varphi) - r^2)^{1/2} + d_L + d_F$, wherein $d_L$ defines a minimum thickness of the volume to be removed.

18. The apparatus of claim 13, wherein the control device is further configured such that the origin is located at the center of the volume.

19. The apparatus of claim 1, wherein the control device is further configured to specify specified target points to the scanner which specified target points are located along a path extending via the specified target points and wherein the apparatus is further configured to emit pulses of the pulsed treatment laser radiation into the eye also to additional intermediate points located on said path between the specified target points.

20. The apparatus of claim 18, wherein the laser device emits the pulses of the pulsed treatment laser radiation into the eye at a frequency $f_p$ and the control device is further configured to supply the target points to the scanner at a frequency $f_s$ which is smaller than the frequency $f_p$.

21. The apparatus of claim 19, wherein the control device is further configured to control the scanning device by a control signal, wherein a maximum frequency of the control signal is smaller than the frequency $f_p$.

22. A method for ophthalmic surgery of an eye of a patient, comprising:
emitting treatment laser radiation;
focusing the treatment laser radiation to a focus position located in the eye;
shifting the focus position in the eye in a pattern of target points located within the eye such that a cut is generated within the eye, wherein a scanner is utilized to shift the focus position in the eye and the target points are specified to the scanner; and
introducing a point of aim in form of a pre-offset for at least some of the specified target points which point of aim differs from a desired final focus position by a spatial difference selected to compensate for focus position errors generated by the focusing device,
wherein the spatial difference depends on the position of the respective target point.

23. The method of claim 22, further comprising providing a correction table or function which indicates the focus position error as a function of the position of the respective target point.

24. The method of claim 22, further comprising shifting the point of aim against the desired final focus position in parallel with the optical axis by the spatial difference.

25. The method of claims 23, further comprising selecting the correction table or function to depend only on axial and radial coordinates (r, z).

26. The method of claim 22, further comprising
defining a path along which the focus position is to be shifted;
defining the pattern by selecting selected points located on the path as target points, and
determining the spatial differences for the selected points.

27. The method of claim 25, wherein defining the path further comprises specifying the path by at least one functional equation and determining the target points by evaluation of said at least one functional equation.

28. The method of claim 22, further comprising taking a deformation of the eye into consideration, which deformation occurs during irradiation of the laser radiation, due to a contact glass pressed onto the eye.

29. The method of claims 26, further comprising first defining the path relating to the eye in an undeformed state and then modifying said path so as to compensate for the deformation of the eye.

30. The method of claims 28, further comprising first defining the path relating to the eye in an undeformed state and then modifying said path so as to compensate for the deformation of the eye.

31. The method of claim 22, further comprising
utilizing a contact glass deforming a front face of the eye into a sphere;
providing focus position data for a shape of a cut to be generated in the eye, which shape is defined for the front face of the eye in a natural and undeformed state, and
transforming the focus position data to compensate for the deformation of the front face of the eye by the contact glass.

32. The method of claim 31, wherein transforming the focus position data comprises keeping an arc length, a radial depth and an angle unchanged.

33. The method of claim 22, further comprising:
creating the cut to isolate a volume in the cornea, and
removing said volume from the cornea causing a change in radius of curvature to an anterior corneal cut surface to correct defective eyesight,
wherein the changed radius of curvature $R_{cv}^*$ satisfies the equation $$R_{CV}^* = 1/((1/R_{CV}) + B_{BR}/((n_c - 1)(1 - d_{HS} \cdot B_{BR}))) + F,$$

wherein $R_{CV}$ is the radius of curvature of the anterior corneal cut surface before removal of the volume, $n_c$ is a refractive power of material of the cornea, F is a correction factor, $B_{BR}$ is a refractive power of spectacles suitable for correction of the defective eyesight, and $d_{HS}$ is a distance at which the spectacles having the refractive power $B_{BR}$ should be located anterior of a corneal vertex in order to achieve the desired correction of defective eyesight by use of the spectacles.

34. The method of claim 33, wherein:
$F = (1 - 1/n_c) \cdot (d_c^* - d_c)$ holds true, wherein $d_c$ is the thickness of the cornea before removal of the volume, $d_c^*$ is the thickness of the cornea after removal of the volume, and
the control device is further configured to calculate the radius $R_{CV}^*$ iteratively by deriving a change in thickness $(d_c^* - d_c)$ from difference $(R_{CV}^* - R_{CV})$ in each iteration step, and by applying the result thus obtained for the change in thickness, when calculating $R_{CV}^*$ in a next iteration step.

35. The method of claim 33, wherein, in order compensate for a cylindrical eyesight defect of the eye (3), the radius $R_{CV}^*$ is a function of a cylindrical angle $\Phi$, i.e. $R_{CV}^*(\Phi) = 1/((1/R_{CV}(\Phi)) + B_{BR}(\Phi)/((n_c - 1)(1 - d_{HS} \cdot B_{BR}(\Phi)))) + F$ holds true.

36. The method of claim 33, wherein the cut confines the volume by a boundary surface, which comprises an anterior cut part and a posterior cut part, wherein the anterior cut part is located at a constant spacing $d_F$ from the anterior corneal surface, but the posterior cut part is not.

37. The method of claim 33, wherein the posterior cut part is curved and has a radius of curvature satisfying $R_L = R_{CV}^* - d_F$.

38. The method of claim 37, wherein the posterior cut part, in cylindrical coordinates $(z, r, \varphi)$ having an origin located at the point where an axis of vision of the eye passes through the anterior corneal face, satisfies the equation $Z_L(r,\Phi) = R_L(\varphi) - (R_L^2(\varphi) - r^2)^{1/2} + d_L + d_F$, wherein $d_L$ defines a minimum thickness of the volume to be removed, which is preferably located at the center of the volume.

39. The method of claim 22, further comprising
  specifying the target points to be located along a path extending via the specified target points, and
  emitting pulses of the pulsed treatment laser radiation into the eye also to additional intermediate points located on said path between the specified target points.

40. The method of claim 39, further comprising utilizing a scanner to shift the focus position, and emitting the pulses of the pulsed treatment laser radiation into the eye at a frequency $f_p$ and supplying the target points to the scanner a frequency $f_s$, which is smaller than the frequency $f_p$.

41. The method of claim 40, further comprising controlling the scanner by a control signal, wherein a maximum frequency of the control signal is smaller than the frequency $f_p$.

* * * * *

UNITED STATES PATENT AND TRADEMARK OFFICE
CERTIFICATE OF CORRECTION

PATENT NO. : 10,390,994 B2
APPLICATION NO. : 16/160490
DATED : August 27, 2019
INVENTOR(S) : Wiechmann et al.

Page 1 of 1

It is certified that error appears in the above-identified patent and that said Letters Patent is hereby corrected as shown below:

In the Specification

Column 15, Line 54, delete "$(d_C * d_C)$" and insert --$(d_C* - d_C)$--

Column 25, Line 35, delete the existing formula and insert the following:
--$R_{CV}* = 1 / ((1/R_{CV}) + B_{BR} / ((n_c-1)(1 - d_{HS} \cdot B_{BR}))) + F$--

Column 26, Line 8, delete the existing formula and insert the following:
--$B_{CV}* = B_{CV} + B_{BR} / (1 - B_{BR} \cdot d_{HS})$--

Column 31, Line 54, delete the existing formula and insert the following:
--$r(t) = [d_S \cdot f_L \cdot d_T \cdot t/\pi - (d_S \cdot f_L \cdot d_T \cdot t)^2 / (2\pi \cdot R_F)^2]^{1/2}$--

Signed and Sealed this
Third Day of March, 2020

Andrei Iancu
*Director of the United States Patent and Trademark Office*